United States Patent [19]

Iwu et al.

[11] Patent Number: 5,290,553
[45] Date of Patent: Mar. 1, 1994

[54] ALKALOIDS OF PICRALIMA NITIDA USED FOR TREATMENT OF PROTOZOAL DISEASES

[75] Inventors: Maurice M. Iwu, Silver Spring; Daniel L. Klayman, Chevy Chase; Joan E. Jackson, Rockville, all of Md.; John D. Tally, Washington, D.C.; Steven L. Andersen, Silver Spring, Md.

[73] Assignee: The United States of America as represented by the Secretary of the Army, Washington, D.C.

[21] Appl. No.: 733,021

[22] Filed: Jul. 22, 1991

[51] Int. Cl.$^5$ .................. A61K 35/78; A61K 31/44
[52] U.S. Cl. .................. 424/195.1; 514/280; 514/282; 514/410; 514/453; 546/50; 548/418; 549/382; 549/456
[58] Field of Search .............. 514/210, 214, 280, 282, 514/183, 410, 449, 468, 453; 546/50; 548/418; 549/382, 456; 540/450, 461

[56] References Cited

PUBLICATIONS

T. A. Henry et al., J. Chem. Soc. 1927 pp. 1950–1959.
T. A. Henry et al., J. Chem. Soc. 1932, pp. 2759–2768.
E. Schlittler, et al., Helv. Chim. Acta. 35:29–45, 1952.

*Primary Examiner*—John W. Rollins
*Attorney, Agent, or Firm*—Werten F. W. Bellamy; John Francis Moran

[57] ABSTRACT

A method of preparing substantially purified alkaloids from seeds, stems, fruit-rind and bark of a plant selected from *Picralima nitida, Gongronema latifolia, Dorstenia multiradiata, Cola attiensis, Rothmania withfieldii* and *Desmodium gangeticum*, for use in the treatment of protozoal diseases, comprising:

pulverizing said plant;

a first solvent, drying the extracted material and re-extracting the dried material with a different solvent;

extracting a fresh sample of said plant with boiling water;

filtering and concentrating the boiling water solvent extracts under reduced pressure;

concentrating the dried extract to a gum and re-extracting said gum with an aqueous acidic HCl solution;

filtering the acidic extract and making it alkaline to a pH of about 9 with a concentration NaOH solution;

extracting the alkaline solution with dichloromethane;

concentrating organic layers of the extracted alkaline solution to dryness under reduced pressure to obtain an alkaloid fraction; and separating the alkaloid fraction by liquid chromotography-mass spectrometry to obtain substantially purified alkaloids for use in treatment of protozoal diseases.

25 Claims, 6 Drawing Sheets

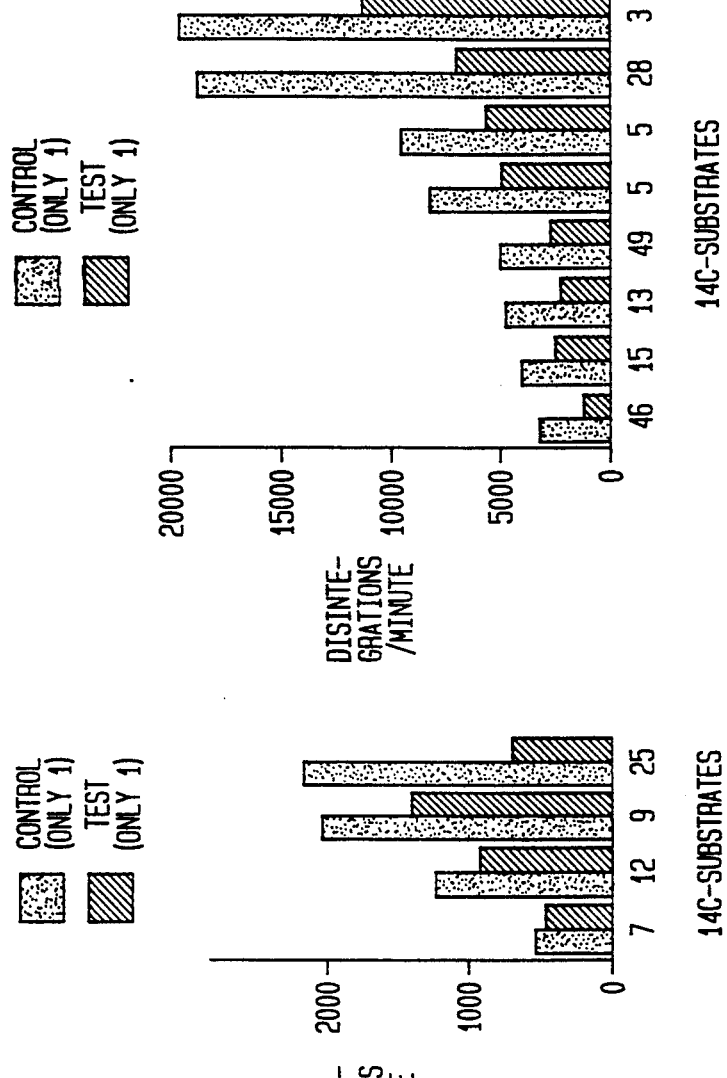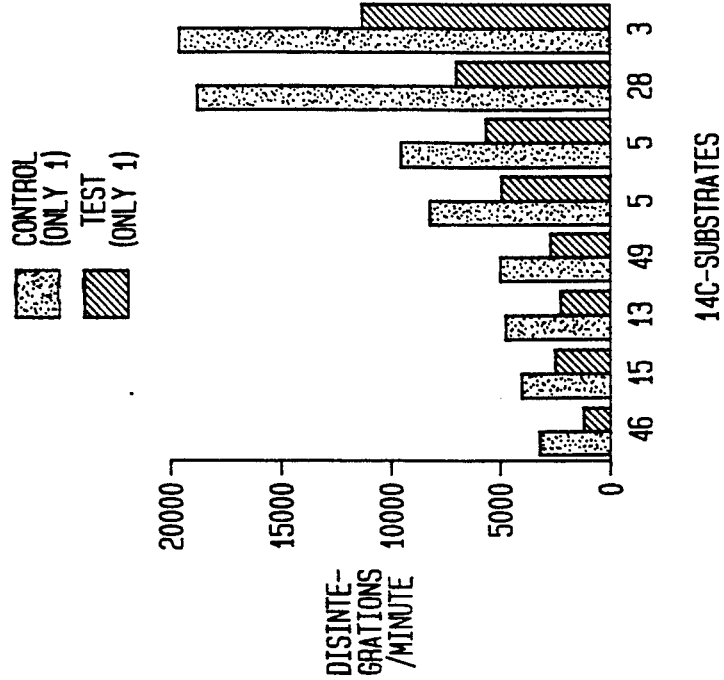

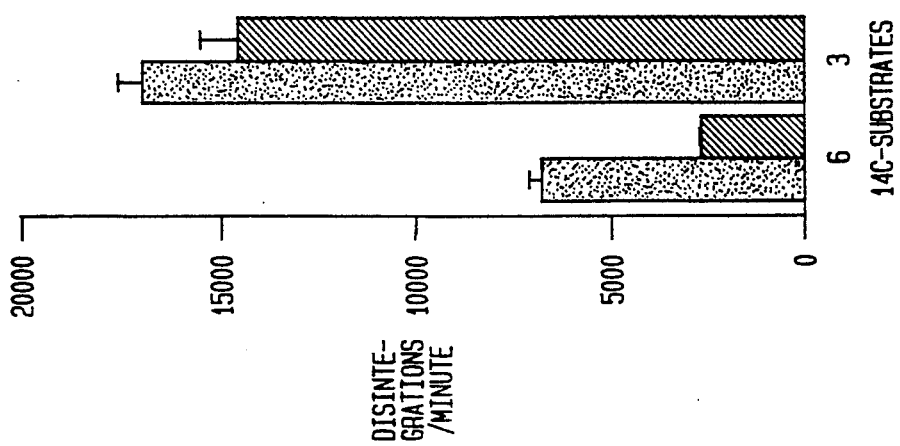
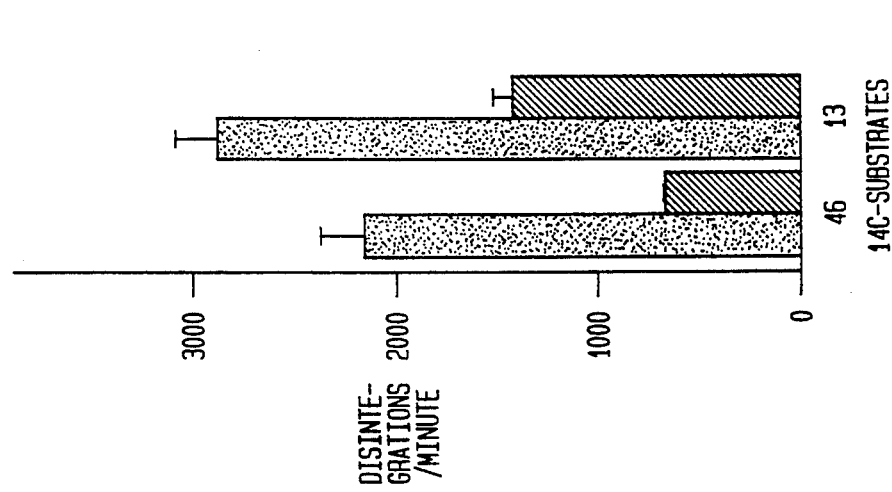
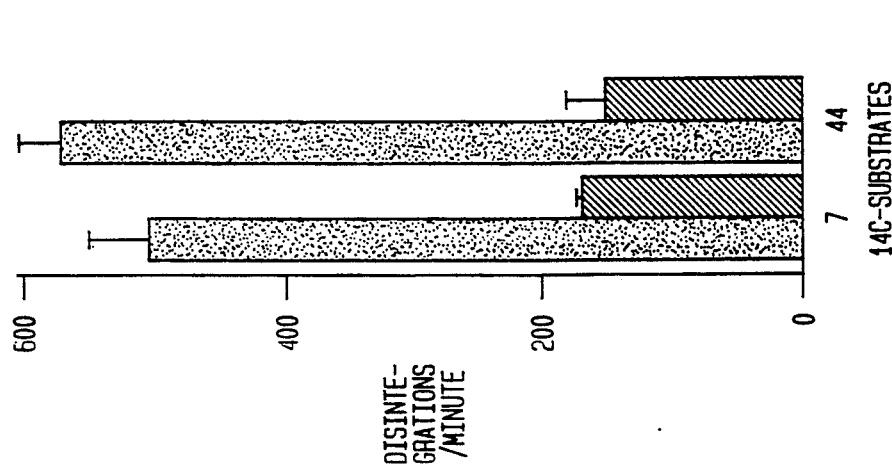

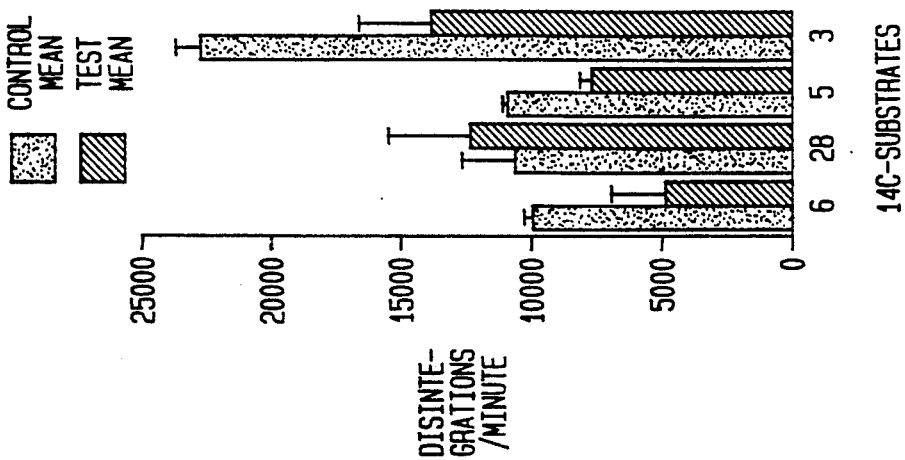
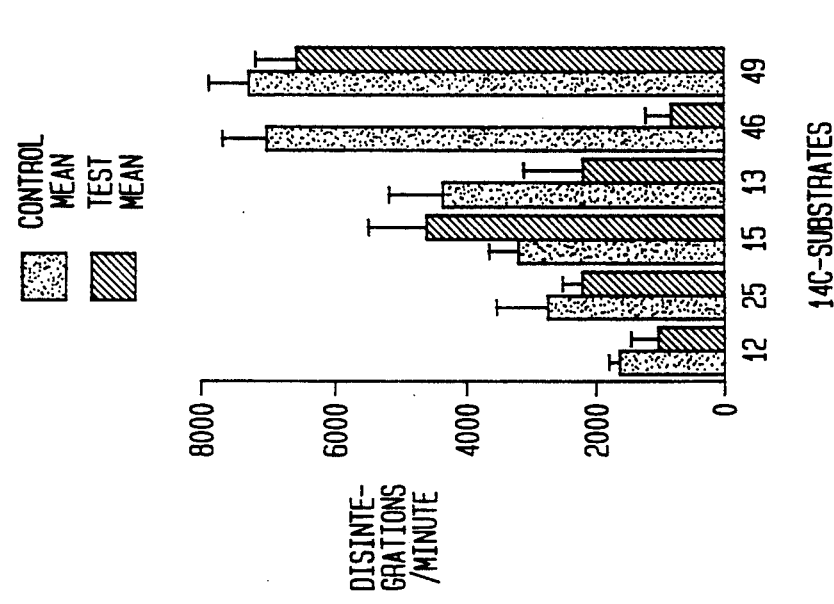
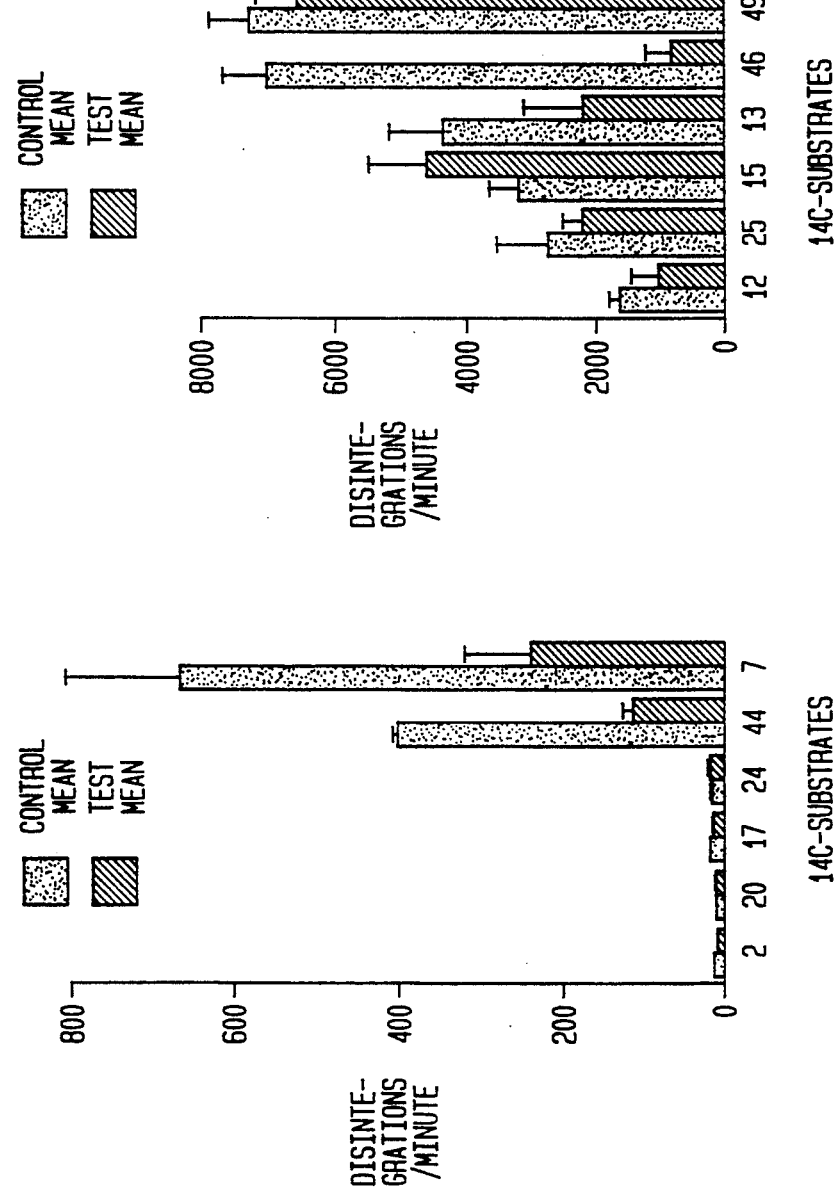

ALKALOIDS OF PICRALIMA NITIDA USED FOR TREATMENT OF PROTOZOAL DISEASES

BACKGROUND OF THE INVENTION

1. Field of the Invention

The invention pertains to extracts of *Picralima nitida* seeds, fruit rind and stem bark, and the use of these extracts in the treatment of malaria, leishmaniases and trypanosomosis.

The alkaloid extracts of the fruits of *P. nitida* exhibit activity against drug-resistant and drug-sensitive malarial strains of *Plasmodium falciparum* and these alkaloids show significant inhibitory activity against both clones of *P. falciparum* at $IC_{50}$ values of 0.0.1-0.9 µg/ml.

The invention also pertains to the use of methanol extracts from *Picralima nitida* for use in the treatment of leishmaniases.

2. Description of the Prior Art

*Picralima nitida* (Fam. Apocynaceae) is the source of the bitter tasting "Akuamma" seeds, employed extensively in west Africa as an ingredient in many folk remedies[1,2]. The aqueous extract of the bark and seeds are used for the treatment of malaria and pyrexia, and the powdered seeds have been dispensed as a cure for pnumonia and other infections[3].

[1] Irvine, F. R. (1961) *Woody Plants of Ghana*, Oxford University Press, London. pp.629-630.
[2] Oliver-Bever, B. (1982) Medicinal plants in tropical west Africa 1. Plants acting on the cardiovascular system, *J. Ethnopharmacol* 5, 1-72.
[3] Ainslie, J. R. (1937) *List of Plants Used in Native Medicine in Nigeria*, Imperial Forestry Institute, Oxford. p.71.

The plant *Picralima nitida* contains several indole and dihydroindole alkaloids, of which the major ones include akuammiline, akuammidine, akuammine, akuammigine, akuammicine, picraline and picraphylline[4,5]. The principal alkaloid found in the plant, akuammine, has been shown to be inactive against avian malaria and in clinical trials[6].

[4] Saxon, J. E. (1973) Alkaloids of Picralima and Alstonia species. In: R. H. F. Manske (ed.), The alkaloids - Chemistry and physiology. Academic Press, New York. p. 157-159.
[5] Ansa-Asamoah, R., Kapadia, G. J., Lloyd, H. A. and Sokoloski, E. A. (1990) Picratidine, A new indole alkaloid from *Picralima nitida* seeds, *J. Nat. Prod.*, 53(4), 975-977.
[6] Paris, R. and Moyse, H. (1971) Precis de Matiere Medicale, vol.3, Masson, Paris, cited in Bep-Oliver, op cit.

Akuammine, however, is a strong sympathicomimetic and possesses local anesthetic action comparable to that of cocaine[7].

[7] Raymond-Hamet, R. (1951) Sur une drogue remarquable de l'Afrique tropicale, le *Picralima nitida* (stapf) Th. & R. Dur. *Revue de Botanique. Appliquee* 31, 465.

Another major Picralima alkaloid, akuammidine has been shown to possess a strong local anaesthetic action and was found to be three times as active as cocaine hydrochloride[8]. The compound also has sympatholytic and a mild, but persistent, hypotensive effect. Extracts of the plant have been shown to posses significant analgesic activity in the rat pedal model[9]. The hot water decoction of the stem bark has been shown to possess significant in vivo activity against *Trypanosoma brucei* in rats, and the activity was found comparable to the effect of 8 mg kg$^{-1}$ of dimenazene aceturate (Wosu and Ibe, 1989). A CNS active indole alkaloid, pericine, has been detected by opiate receptor binding studies from the cell suspension culture of *P. nitida*[10]. Although seeds and stem bark of *P. nitida* are employed as aqueous ethanol (palm wine) decoctions in the treatment of severe cases of malaria in Nigeria, Ghana and many parts of Africa, there is presently no scientific investigation to support the use of the herb as a malaria remedy.

[8] Raymond-Hamet, R. (1944) *Picralima nitida*. These Doc. Pharm., Paris.
[9] Ezekwesili, J. (1983) Pharmacological activity of *Picralima nitida*, M. Pharm Dissertation, University of Nigeria, Nsukka.
[10] Arens, H., Borbe, H. O. Ulbrich, B. and Stockigt, J. (1982), Detection of pericine, a new CNS-active indole alkaloid, *Planta Med.* 46(4). pp. 210-214.

Infections due to protozoa of the genus Leishmania are a major world-wide health problem, with high endemicity in developing countries, however, the global prevalence of leishmaniases in man is about 12 million cases, with an estimated incidence of 2-3 million cases per annum[11]. The pathological effects of the disease are complex and manifests in various forms ranging from self-healing cutaneous lesions; recurrent leishmaniasis recidivans; disfiguring mucocutaneous and diffuse cutaneous diseases; to fatal systemic infection, visceral leishmaniases or kala azar. In the later form, the reticuloendoethelial system is infected with the resultant toll on the spleen, liver, bone marrow, lymph glands, and, often, some degree of intestinal tract dysfunction. Approximately 350 million people within 80 countries are threatened by the disease worldwide.

[11] World Report on Tropical Diseases. WHO Features 139 (March, 1990): 1-12.

Unfortunately, clinical drug intervention is presently limited to the use of pentavalent antimonials (SbV), sodium stilbogluconate and N-methylglucamine antimonate, and, secondarily, amphotericin or pentamidine[12,13]. These antileishmanials require parenteral administration with clinical supervision or hospitalization during treatment because of the severity of possible toxic side-effects that include cardiac and/or renal failure[14].

[12] Bryceson, A. (1987) Therapy in man. Peters, W., Killick-Kendrick, R., eds., *The Leishmaniases in Biology and Medicine*, Vol. 2, New York: Academic Press, pp. 847-907.
[13] Croft, S. L. (1988) Recent developments in the chemotherapy of leishmaniasis. Trends Pharmacol Sci 9:376-381.
[14] Bryceson, A. (1987) Therapy in man. Peters, W., Killick-Kendrick, R., eds, *The Leishmaniases in Biology and Medicine*, Vol. 1, New York: Academic Press, pp. 847-907.

Treatment with the aforementioned agents is not consistently effective particularly for the most virulent leishmanial disease forms[15,16,17,18]. The World Health Organization has reported large scale resistance of kala azar to SbV, which are the preferred chemotherapy for treatment of most forms of leishmanial disease (TDR News, Dec., 1990). In some endemic regions, it has been observed that prolonged medication (22 months or more) with SbV is required to effect a clinical cure[19]. Long term SbV therapy, however, is not usually advocated due to the mentioned cardiac and renal toxicity of SbV.

[15] Jha, T. K. (1983) Evaluation of diamidine compound (pentamidine isethionate) in the treatment of resistant cases of kala azar occurring in North Bihar, India. Trans Roy Soc Trop Med Hyg 77:167-170.
[16] Rocha, R. A., Sampaio, R. N., Guerra, M., Magalhaes, A., Cuba, C. C., Barreto, A. C., Marsden, P. D. (1980) Apparent Glucantime failure in five patients with mucocutaneous leishmaniasis. J Trop Med Hyg 83:131-139.
[17] Mebrahtu, Y. B., Lawyer, P., Githure, J., Were, J. B., Muigai, R., Hendricks, L., Leeuwenburg, J., Koech, D., Roberts, C. (1989) Visceral leishmaniasis unresponsive to pentostam caused by *Leishmania tropica* in Kenya. Am J Trop Med Hyg 41:289-294.
[18] Anonymous (1990) Antimonials: large-scale failure in leishmaniasis "alarming". Trop Dis Rsch News (World Health Organization Special Program for Research and Training in Tropical Diseases) 34:1&7.
[19] Bryceson, A. (1987) Therapy in man. Peters, W., Killick-Kendrick, R., eds, *The Leishmaniases in Biology and Medicine*, Vol. 2, New York: Academic Press, pp. 847-907.

There is, therefore, a need for the development of more effective, less toxic and orally active antileishmanial agents. However, development of a new drug for the treatment of leishmaniasis has been impeded by the lack of a simple, rapid and universally applicable (to the various Leishmania species/strains infecting humans) drug evaluation system[20,21]. The lack of progress in the development of new antileishmanial agents is evident by the fact that all the clinically useful drugs were developed between 1947 and 1959[22]. Current methods for screening potential antileishmanial agents generally utilize intracellular amastigotes (the mammalian intracellular form) since promastigotes (monoflagellate forms found within the insect vector and culture in vitro) are reported "insensitive" within in vitro assays to SbV compounds used for human leishmaniases[23]. Since there is no system yet available for culturing amastigotes extracellularly except re-isolation from infected tissues and macrophage cultures, their mass culture is rather limited[24,25], thereby making them unsuitable for primary screening of potential antileishmanial agents.

[20] Croft, S. L. (1986) In vitro screens in the experimental chemotherapy of leishmaniasis and trypanosomiasis. Parasit Today 2:64–69.
[21] Neal, R. A. (1987) Experimental chemotherapy. Peters, W., Killick-Kendrick, R., eds, The Leishmaniases in Biology and Medicine, Vol 2, New York: Academic Press, pp. 793–845.
[22] Jackson, J. E., Tally, J. D., Tang, D. B. (1989) An in vitro micromethod for drug sensitivity testing of Leishmania. Am J Trop Med Hyg 41:318–330.
[23] Ibid.
[24] Ibid.
[25] Croft, S. L. (1986) In vitro screens in the experimental chemotherapy of leishmaniasis and trypanosomiasis. Parasit Today 2:64–69.

An in vitro radiorespirometric microtest using promastigotes has been developed which relies on drug inhibition of parasite production of $^{14}CO_2$ or $^3H_2O$ Etery of $^{14}C$-substrates by promastigotes to detect drug-mediated parasite damage at low drug concentration within a short time[26,27]. The test is quantitative, rapid, consistent, and conducted in a serum-free chemically defined medium in which prior adaptation is not necessary to cultivate the so-called "difficult to grow" species. The method has been shown to correlate to patients response to SbV therapy[28].

[26] Jackson, J. E., Tally, J. D., Tang, D. B. (1989) An in vitro micromethod for drug sensitivity testing of Leishmania. Am J Trop Med Hyg 41:318–330.
[27] Jackson, J. E., Tally, J. D., Ellis, W. Y., Membrahtu, Y. B., Lawyer, P. G., Were, J. B., Reed, S. G., Panisko, D. M., Limmer, B. L. (1990) Quantitative in vitro drug potency and drug susceptibility evaluation of leishmania spp. from patients unresponsive to pentavelent antimony therapy. Am J Trop Med Hyg 43:464–480.
[28] Ibid.

Visceral leishmaniasis is endemic to the central Nigerian highlands, and zoonotic cutaneous leishmaniasis, prevalent in the northern half of this country. Therefore, because of limited supply, expense and toxicity of commercial antileishmanials, traditional herbal therapy is frequently utilized in many leishmanial endemic regions of Nigeria.

SUMMARY OF THE INVENTION

It is an object of the invention to procure extracts of Picralima nitida seeds, fruit rind, and stem bark and utilize these extracts for anti-malarial activity or inhibitory activity against drug-resistant clones of Plasmodium falciparum.

A further object of the invention is to provide water, methanol or dichloromethane extracts of Picralima nitida seeds, fruit rind and stem bark for anti-malarial activity or inhibitory activity against drug-resistant clones of Plasmodium falciparum.

A yet further object of the invention is to provide water, methanol or dichloromethane extracts of alstonine, akuammine, akuammicine, melinonine, picraphylline, picraline, and pseudo-akuammigine isolated from the fruits and stem of Picralima nitida as active constituents or ingredients for anti-malarial activity or inhibitory activity against drug-resistant clones of Plasmodium falciparum.

A still further object of the invention is to provide dimers (compounds formed from the combination of isolates of alstonine, akuammine, akuammicine, melinonine, picraphylline, picraline, and pseudo-akuammigine) for example, serpentinine, as active constituents or ingredients for anti-malarial activity or inhibitory activity against drug-resistant clones of Plasmodium falciparum.

A further object still of the invention is to provide methanol and aqueous extracts of Picralima nitida to provide inhibition of leishmania promastigotes.

A yet further object of the invention is to provide methanol and aqueous extracts of Picralima nitida which are sufficiently active at certain concentrations against visceral Leishmania chagasi and cutaneous L. mexicana.

A further object still of the invention is to provide the indole alkaloids akuammine, pseudo-akuammigine, picraline, alstonine and akuammicine isolated from the active fraction for inhibition of leishmania promastigotes.

A still further object of the invention is to provide extracts and isolates from Picralima nitida and Dorstenia multiradiata for treatment of trypanosomiases where other chemotherapeutic agents are generally unsatisfactory due to very high toxicity of these other chemotherapeutic agents or the drug resistance of Trypanosoma brucei.

A further object still of the invention is to provide methanol and aqueous extracts of Picralima nitida seeds or Dorstenia multiradiata to provide antitrypanosomial activity.

A still further object of the invention is to provide the indole alkaloids akuammine, pseudo-akuammigine, picraline, alstonine and akuammicine isolated from the active fraction of P. nitida and anthocyanidins as the active components of the extract from D. multiradiata as agents for antitrypanosomial activity.

Anti-malarial activity using water, methanol or dichloromethane extracts of Picralima nitida seeds, fruit rind and stem bark is obtained against drug-resistant clones of plasmodium falciparum at dosages between about 1.23 to 32 $\mu g/ml$.

Inhibition of leishmania promastigotes is accomplished by using methanol and aqueous extracts of Picralima nitida. By using radiorespirometric microtests based on in vitro inhibition of catabolism of $^{14}CO_2$ of a battery of $^{14}C$-substrates by promastigotes, these extracts are active at concentrations of 50 $\mu g/ml$ or less against visceral Leishmania chagasi and cutaneous L. mexicana. These extracts significantly inhibited (10%–90%) of the catabolism of certain sugars, amino acids, or fatty acid precursors by promastigotes. The indole alkaloids akuammine, pseudo-akuammigine, picraline, alstonine and akuammicine were isolated from the active fraction; however, the greatest inhibition is with alstonine. Alstonine exhibited a dose related activity with the highest growth inhibition being at 50 $\mu g/ml$. At 20 $\mu g/ml$ the alstonine compound showed a growth of 69.3% after 96 hours.

Extracts from Picralima nitida and Dorstenia multiradiata are active at very low doses in the treatment of trypanosomiasis by using a dose of 50 mg/kg and 5 mg/kg of the methanol and aqueous extracts respectively of Picralima seeds. These doses completely cleared animals of the parasites at post-treatment day 12 in rats and day 10 in a mouse model. Methanol extract of Dorstenia gave similar results at treatment day 10 and 8 for the rat and mouse models respectively. The indole alkaloids akuammine, pseudo-akuammigine, picraline, alstonine and akuammicine were isolated from the active fraction of *Picralima nitida*, whereas anthocyanidins were the active components of the extract from *Dorstenia multiradiata*.

BRIEF DESCRIPTION OF THE DRAWINGS

FIGS. 4(A),(B),(C) show a radiorespirometric microtest based on in vitro inhibition of catabolism of $^{14}CO_2$ of a battery of $^{14}CO_2$ substrates by promastigotes, used to examine extracts of plants for antileishmanial activity; wherein Gongronema (GG) displayed strong inhibition of the catabolism of succinic acid, D-galactose, D-mannose, L-aspartic acid, L-glutamine and D-glucosamine, as well as L-proline, Na-n-butyric acid, and L-glutamic acid. The GG-8 is highly active against the etiologic agent of visceral leishmaniasis, *Leishmania* (*Leishmania*) *chagasi*.

FIGS. 5(A),(B),(C) depict the activity for succinic acid, glycine and aspartic acid, where an inhibition rate of 40% or more is obtained with glutamic acid, glutamine and methionine.

FIGS. 6(A),(B),(C) show the extract of Dorstenia strongly inhibited the catabolism of ornithinie, butyric acid and mannose.

DETAILED DESCRIPTION OF THE INVENTION

Materials and Methods

Figure 1:
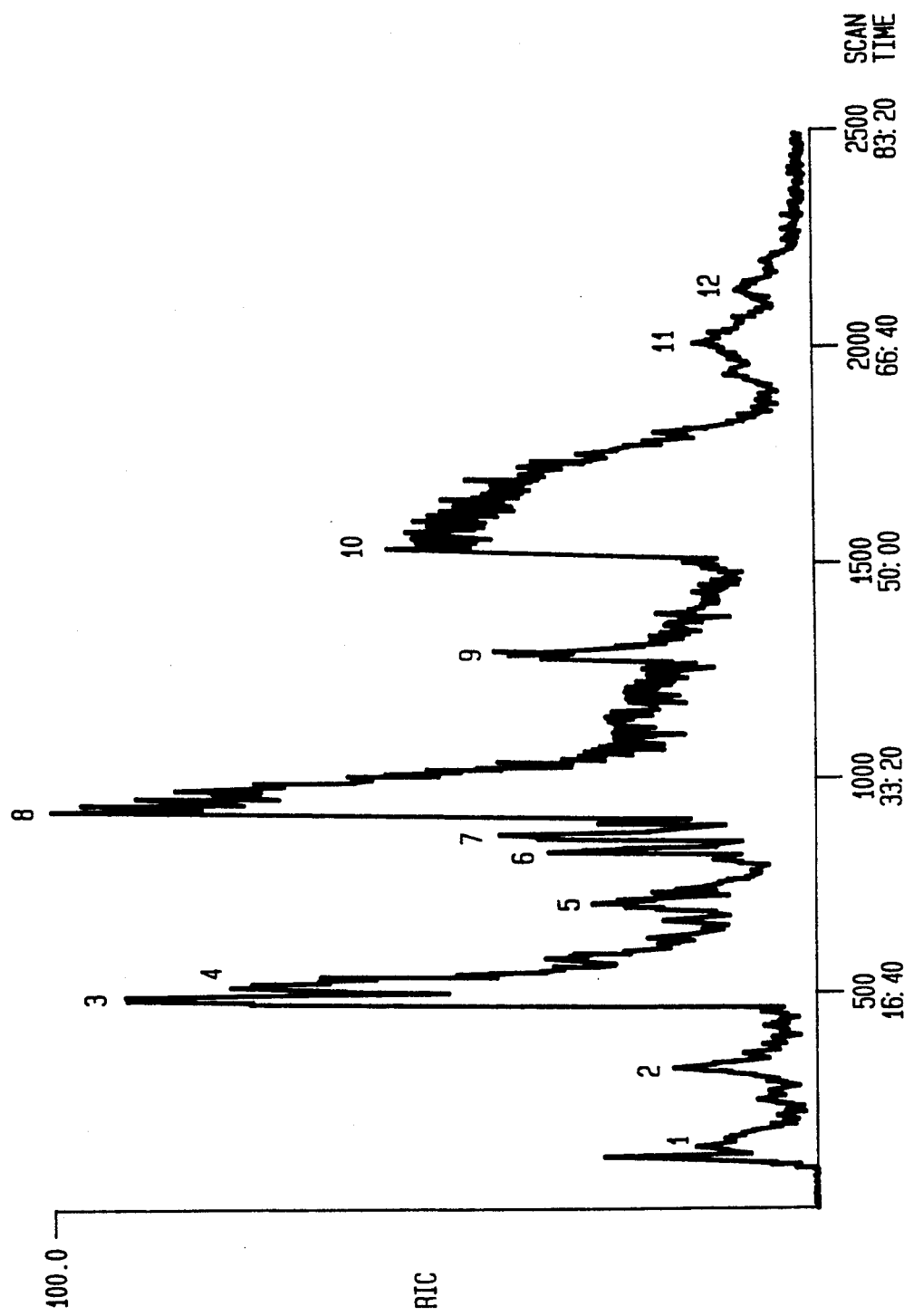
FIG. 1 depicts a thermal spray liquid chromatogram of the dichloromethane extract of *P. NITIDA* fruit rind.

*P. nitida* fruits were collected from trees at a homestead in Anambra state, Nigeria. The seeds and the fruit-rind were separated and air-dried. The stem bark was obtained from the branch of a tree at the above location. Each plant part was cut into small pieces and powdered.

Extraction

Powdered seeds of *P. nitida* (500 g) were extracted with 5 $CH_2Cl_2$ in a Soxhlet extractor for 10 hours. The seeds was air dried and re-extracted with 5 l of MeOH for about 6 hours. A fresh sample of the seeds (200 g) was extracted with boiling water for 6 hours. The extracts were filtered and concentrated to dryness under reduced pressure, and the aqueous fraction was freeze-dried. The seed oil was obtained from the petroleum ether (b.p. 40°-60°) extraction of the seeds. The fruit rind (200 g) and the stem bark (100 g) were similarly extracted with $CH_2Cl_2$ and MeOH.

Alkaloid fractionation

The MeOH extract (10 g) of the stem bark (prepared as described above) was concentrated to a sticky gum and re-extracted (for 30 minutes) with 200 ml of 10% HCl. The aqueous acidic extract was filtered, made alkaline to pH 9 with concentrated NaOH solution and extracted with 10×200 ml $CH_2Cl_2$. The organic layers were concentrated to dryness under reduced pressure to yield the alkaloid fraction, which were found to contain several Dragendorff positive spots on TLC. The MeOH extracts of both the fruit rind and the seeds were similarly treated and the combined organic layers were concentrated under reduced pressure.

Authentic samples or reference compounds of akuammine, picratidine, akaummigine and akuammiline (from the University of Science and Technology, Kamasi Ghana), picraline, echitamine, akuammicine and ψ-akuammigine (from Universite de Reims, Champagne-Ardenne, Reims, France), and echitamine (from Laboratoire des Plantes Medicinales du C.N.R.S., B.P. 643 Noumea, New Caledonia) were used as reference compounds.

Antimalarial screening

The in vitro assays were performed by using a modification of the semi-automated microdilution technique described earlier in Desjardins et al.[29] and Milhous et al.[30] Two *P. falciparum* malaria parasite clones, designated as Indochina (W-2) and Sierra Leone (D-6), were utilized in susceptibility testing. The W-2 clone is resistant to chloroquine, pyrimethamine, sulfadoxine, and quinine, and the other clone is resistant to mefloquine. The test extracts were dissolved in dimethylsulfoxide (DMSO) and serially diluted with media. The uptake of tritiated hypoxanthine was used as an index of inhibition of parasite growth.

[29] Desjardins, R. E., Canfield, C. J., Haynes, D. E., Chulay, J. D. (1979) Quantitative assessment of antimalarial activity in vitro by a semiautomated microdilution technique, *Antimicrob. Agents Chemother.* 16, 710-178.
[30] Milhous, W. K., Weatherly, N. F., Bowdre, J. H. and Desjardins, R. E. (1985) In Vitro activities of and mechanism of resistance to antifol antimalarial drugs, *Antimicrob. Agents Chemother.* 27, 525-530.

Liquid Chromatography—Mass Spectrometry of *P. nitada* Extracts

The separation of the constituents of the extracts was conducted on a Varian 5500 liquid chromatograph with a Vista detector. Waters Bodapak $C_{18}$ columns were eluted with $CH_3CN$—$H_2O$ (60:40).

Thermospray liquid chromatography-mass spectrometry (LC-MS) was conducted on a Waters liquid chromatograph interfaced to a Nermag R10-10C quadrupole mass spectrometer equipped with a Nermag thermospray source and Vestec thermospray probe and gradient controler. Data acquisition was by Finnigan Super INCOS data system. The thermospray source was operated at 200° C. with the thermospray probe run at $T_1=105°$ C. and $T_2=190°$ C. No filament, repeller, or discharge current was applied.

The in vitro antimalarial activities of various extracts of *P. nitida* on *P. falciparum* clones are shown in Table 1. All the extracts inhibited the uptake hypoxanthine by the plasmodia at low concentrations, with $IC_{50}$ values ranging from 1.23 μg/mL to 32.16 μg/mL. The $CH_2Cl_2$ extracts (1,4,6) showed the strongest activity when compared to the methanolic (2,5) and aqueous (3) extracts with $IC_{50}$ of 1.61 μg/ml and 5.15 μg/ml for the fruit rind and seeds, respectively, in the W-2 plasmodium clone; and 5.03 μg/ml and 2.4 μg/ml for the respective plant parts in the D-6. The fruit rind (extract 4) had the best activity in the W-2 system while the alkaloidal fraction of MeOH extract (9) of the stem bark gave the best activity in the D-6 system.

Figure 2:
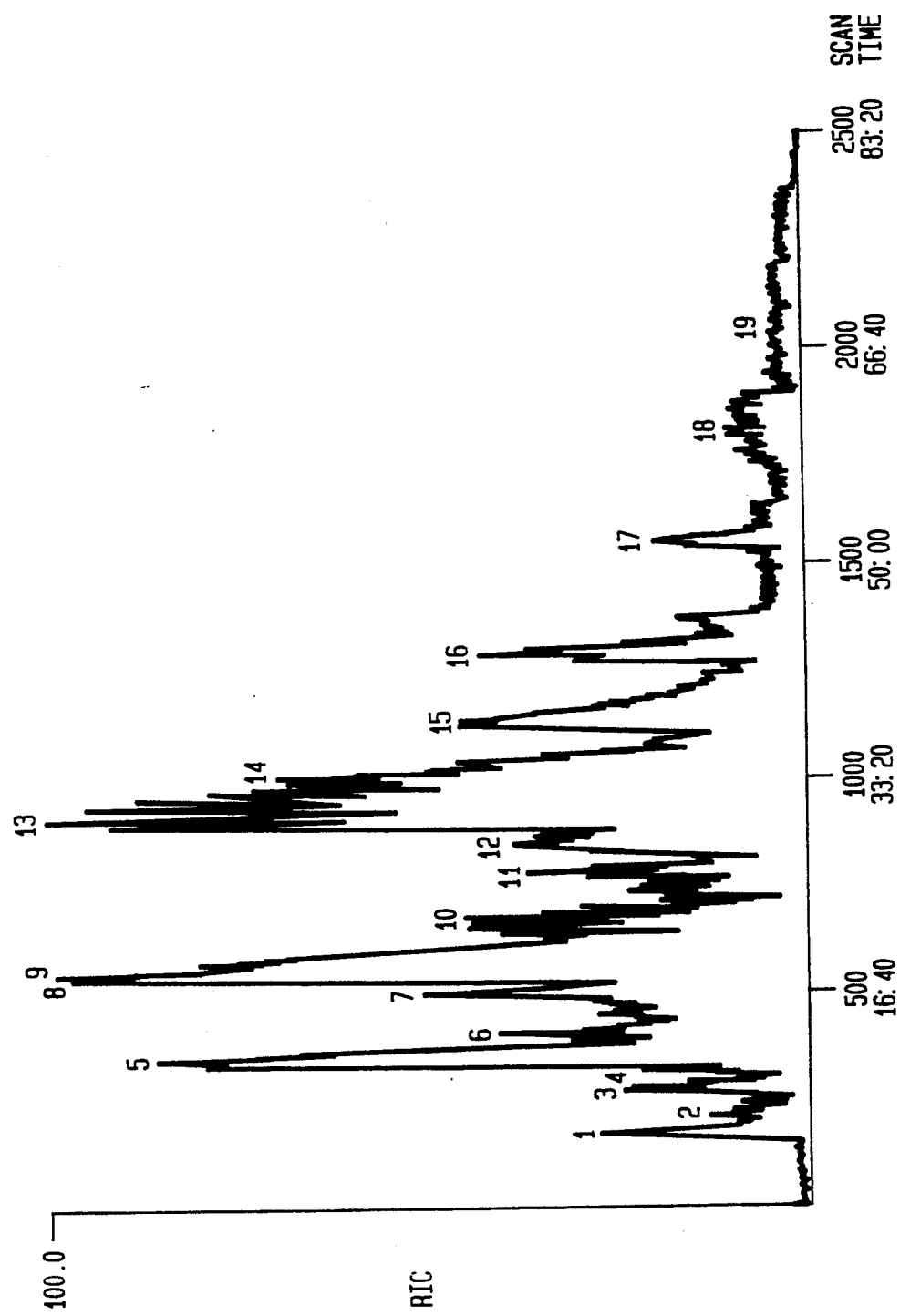
FIG. 2 shows a thermal spray liquid chromatogram of the dichloromethane extract of *P. NITIDA* seed.
Figure 3A:
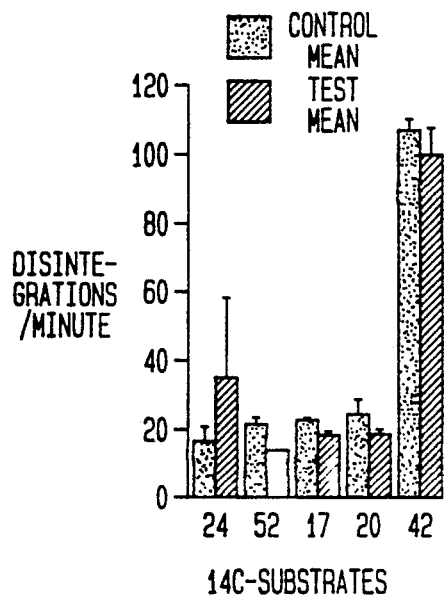
FIGS. 3(A),(B),(C),(D) show a radiorespirometric microtest based on in vitro inhibition of catabolism of $^{14}CO_2$ of a battery of $^{14}CO_2$ substrates by promastigotes used to examine extracts of plants for antileishmanial activity; wherein *Cola attiensis* extract (CT) inhibited parasite catabolism of 5 of the 21 substrates used in the assay, with the strongest activity observed on the disintegration of ornithine, L-proline, L-aspartic acid.
Figure 3B:
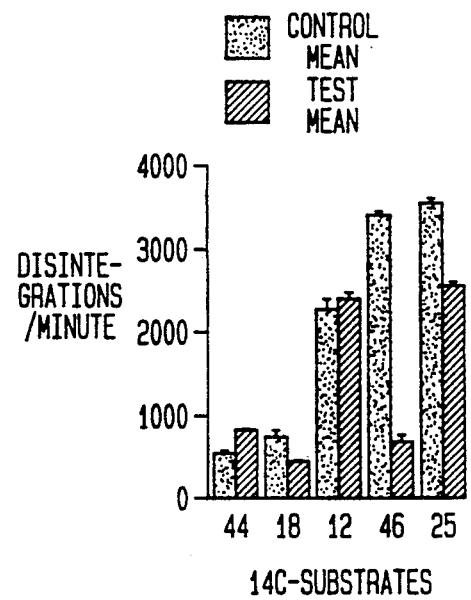
Figure 3C:
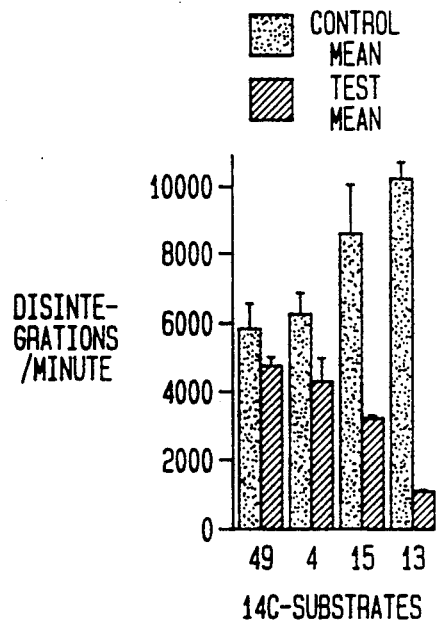
Figure 3D:
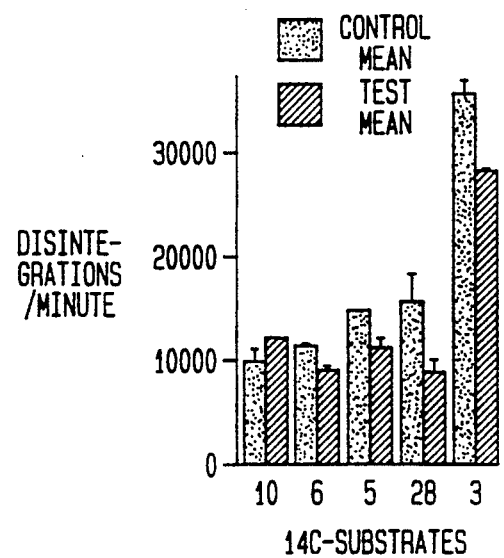

The retention times and major ions obtained from the LC-MS of the $CH_2Cl_2$ extracts of the seeds and fruit rind, the two most active extracts, are shown in Tables 2 and 3. From the molecular ion peaks obtained, it was observed that the common Picralima alkaloids were not detected as major components of the $CH_2Cl_2$ extracts of either the fruit rind or seeds of *P. nitida*. Akuammine (M+1=m/z 383), ψ-akuammigine (M+1=m/z 367) and picraline (M+1=m/z 411) were detected in the fruit rind (Table 2). The only peak corresponding to the molecular weight of a known picralima alkaloid, akuammiline was observed at 9:34 min. (M +1=m/z 395) in the LC-MS chromatogram of the seed (Table 3). These constituents occured as minor components of the extracts (FIG. 1 and 2). The LC of SB1 and SB2 using authentic samples of Picralima alkaloids indicated the presence of akuammine, akuammicine and traces of akuammigine, akuammidine and picratidine. The retention times of the major constituents of the extracts did not correspond to those of any of the reference compounds. Significant differences were observed in the composition of the rind and the seed extracts (FIG. 1 and 2). LC-MS indicated high mass spectra peaks (>500 m/z) not previously reported from this species, which suggests the possibility of novel compounds being the active components.

Results of the in vitro assay show that the extracts of *P. nitida* possessed activity against *P. falciparum* strains. The antimalarial activities of these extracts are superior to those reported for most experimental antimalarial plant and isolates, i.e. Weenen et al[31]; Khalid et al.[32]; Cubukcu et al.[33] The activity of these extracts are apparently weaker (from the relative $IC_{50}$ values) than those of the clinically useful antimalarials of plant origin, quinine (cf. Warhurst[34]) and artemisinin (cf. Klayman[35]). It should be noted, however, that of the test extracts comprised of a mixtureof many compounds, some of the mixtures, in fact, prove to be more active than current antimalarials. It must also be noted that the extracts were active against drug resistant strains of the parasite and this of course indicates a potential for use in cases of drug resistant malaria chemotherapy.

[31] Weenen, H., Nkunya, M. H. H., Bray, D. H., Mwasumbi, L. B., Kinabo, L. S. and Kilimali, V. A. E. B. (1990) Antimalarial of Tanzanian medicinal plants, Planta Med. 56, 368–370.
[32] Khalid, S. A., Farouk, A., Geary, T. G., and Jensen, J. A. (1986) Potential antimalarial candidates from African plants: an in vitro approach using *Plasmodium falciparum*. J. Ethnopharmacol. 15, 201–209.
[33] Cubukcu, B., Bray, D. H., Warhurst, D. C., Mericli, A. H., Ozhatay, N. and Sariyar, G. (1990) In vitro antimalarial activity of crude extracts and compounds from *Artemisia abrotanum* L, Phytother. Res. 4 (5), 203–204.
[34] Warhurst, D. C. (1985) Natural and Biosynthetic Products as Potential Antiparasitic Agents, In: Advances in Medicinal Plant Research, Wissenschaftliche Verlagsgesellschaft mbH, Stuttgart, p.33–46.
[35] Klayman, D. L. (1985) Qinghaosu (Artemisinin): An antimalarial drug from China, Science 228, 1049–1055.

Fractionation of the extracts, using classical alkaloid separation scheme led to significant improvement in the antimalarial activity. The $IC_{50}$ value of the stem bark was reduced from 6.46 μg/mL for the crude extract to 2.25 μg/mL in the Draggendorf positive fraction when tested against the W-2 clone, and in the D-6 model, the $IC_{50}$ values of 14.86 μg/mL and 1.23 μg/mL were observed for the crude extract and the alkaloid fraction, respectively. While the result suggests the possibility that alkaloids might be active components of this plant, the significant antimalarial activity detected in both seed oil and the aqueous extract indicates a contribution of non-alkaloidal constituents to the anti-malarial activity of Picralima.

It was surprising that known Picralima alkaloids were not detected as the major constituents of the biologically active dichloromethane extracts, although peaks corresponding to akuammine, ψ-akuammigine and picraline were observed as minor constituents. The high molecular weight compounds found in the LC-MS of these extracts appeared to be dimers of the previously identified alkaloids, because, in most cases, the observed molecular ion peaks correspond to the expected mass of such dimeric alkaloids.

TABLE 1

IN VITRO ANTIMALARIAL ACTIVITY OF *PICRALIMA NITIDA* EXTRACTS AGAINST W-2 AND D-6 CLONES OF *PLASMODIUM FALCIPARUM*

| | | | $IC_{50}$ μg/ml | |
|---|---|---|---|---|
| Extract | Plant Part | Solvent | W-2 Clone | D-6 Clone |
| 1 | Seeds | $CH_2Cl_2$ | 5.15 | 5.03 |
| 2 | Seeds | $CH_3OH$ | 7.35 | 12.99 |
| 3 | Seeds | $H_2O$ | 17.40 | 12.15 |
| 4 | Fruit rind | $CH_2Cl_2$ | 1.61 | 2.41 |
| 5 | Fruit rind | $CH_3OH$ | 20.79 | 32.16 |
| 6 | Stem bark | $CH_2Cl_2$ | 6.46 | 14.86 |
| 7 | Seeds | Pet. ether | 22.81 | 25.87 |
| 8 | Seeds | $CH_3OH^a$ | 2.25 | 2.64 |
| 9 | Stem bark | $CH_3OH^a$ | 2.00 | 1.23 |
| 10 | Fruit rind | $CH_3OH^a$ | 2.16 | 1.59 |

[a] Alkaloid fraction

TABLE 2

THERMOSPRAY LIQUID CHROMATOGRAPHY-MASS SPECTROMETRY (LC-MS) OF THE DICHLOROMETHANE EXTRACT *PICRALIMA NITIDA* FRUIT RIND.

| Peak no. | Retention time (Min) | Major ions | M + 1 |
|---|---|---|---|
| 1. | 6:12 | 211(B) | 251 |
| 2. | 11:24 | 369(B) 251 234 210 | 383 |
| 3. | 16:22 | 410 369(B) 368 | 411 |
| 4. | 17:26 | 339(B) 318 | 355 |
| 5. | 22:42 | 738 | 808(B) |
| 6. | 27:50 | 349(B) | 367 |
| 7. | 30:40 | 363 261 | 698(B) |
| 8. | 31:30 | 367 349 | 698 |
| 9. | 43:04 | 349 | 435 |
| 10. | 51:58 | 685 363 318 | 686(B) |
| 11. | 67:06 | 757 686 435 379(B) 365 349 | 793 |
| 12. | 71:14 | 685 526 463 379 351 349 | 701(B) |

TABLE 3

THERMOSPRAY LIQUID CHROMATOGRAPHY-MASS SPECTROMETRY (LC-MS) OF THE DICHLOROMETHANE EXTRACT OF *P. NITIDA* SEED

| Peak no. | Retention time (Min.) | Major ions m/z (B = base peak) | M + 1 |
|---|---|---|---|
| 1. | 6:06 | 274 253 212(B) 198 164 | 360? |

TABLE 3-continued
THERMOSPRAY LIQUID CHROMATOGRAPHY-MASS SPECTROMETRY (LC-MS) OF THE DICHLOROMETHANE EXTRACT OF P. NITIDA SEED

| Peak no. | Retention time (Min.) | Major ions m/z (B = base peak) | M + 1 |
|---|---|---|---|
| 2. | 8:34 | 434<br>390(B)<br>349<br>314<br>299<br>245 | 479 |
| 3. | 9:34 | 394<br>354<br>353(B) | 395 |
| 4. | 12:08 | 756<br>738(B)<br>646<br>387<br>370 | 773 |
| 5. | 12:16 | 752<br>734(B)<br>408<br>385<br>368 | 769 |
| 6. | 14:02 | 385(B)<br>368<br>367<br>355 | 386 |
| 7. | 15:24 | 388<br>389(B)<br>355, 354 | 387 |
| 8. | 18:24 | 371<br>354<br>298 | 386(B) |
| 9. | 18:42 | 644<br>386(B)<br>370<br>354<br>298 | 771 |
| 10. | 20:12 | 357(B)<br>340<br>300<br>259 | 385 |
| 11. | 26:22 | 385<br>370<br>322<br>270 | 429(B) |
| 12. | 28:46 | 366<br>326(B) | 649 |
| 13. | 30:14 | 738<br>414(B)<br>386<br>326 | 737 |
| 14. | 33:54 | 398<br>355(B)<br>327 | 413 |
| 15. | 37:38 | 428<br>410<br>370(B)<br>355 | 444(?) |
| 16. | 43:22 | 413<br>370<br>369(B)<br>355<br>325 | 429 |
| 17. | 51:18 | 412<br>369<br>353 | 413(B) |
| 18. | 59:56 | 401<br>385<br>369(B)<br>325 | 467 |
| 19. | 67:32 | 678<br>648<br>467(B)<br>369 | 723 |

In the context of this invention, we have tested the major alkaloids of the fruits of P. nitida for in vitro activity against drug resistant and drug sensitive strains of Plasmodium falciparum. The alkaloids showed remarkable inhibitory activity against both clones of P. falciparum at $IC_{50}$ values of 0.017–0.9 µg/mL. Among the compounds tested, those belonging to the picraline-akammine subgroup showed the greatest activity, followed by those of the akuammicine type. The alkaloid echitamine showed no activity in this regard.

The structural formulas of the Picralima nitida alkaloids exhibiting in vitro antimalarial activity are as follows:

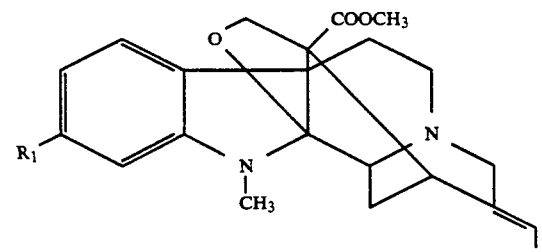

$R_1$ = H, ψ - Akuammigine
$R_1$ = OCH₃, Akuammine

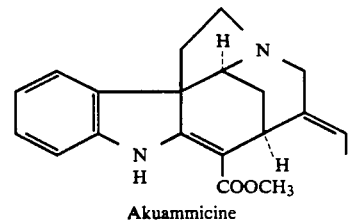

Akuammicine

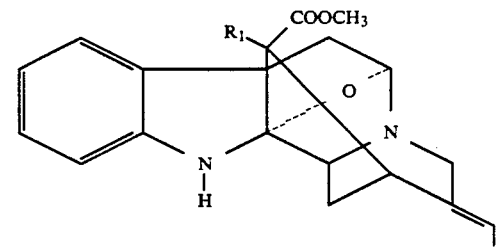

$R_1$ = H, Picrinine
$R_1$ = CH₂OCOCH₃, Picraline
$R_1$ = CHO, Picralinal

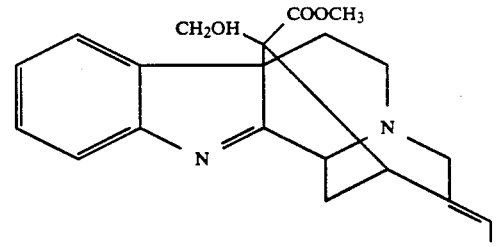

Akuammiline

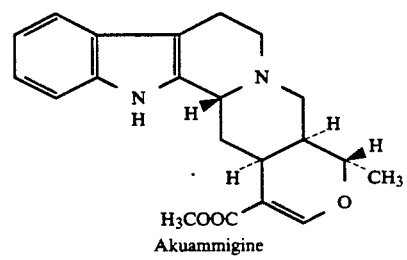

Akuammigine

-continued
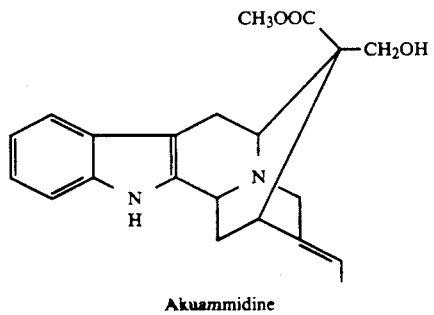
Akuammidine
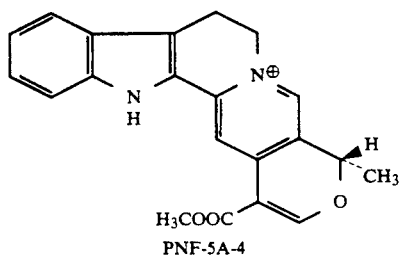
PNF-5A-4
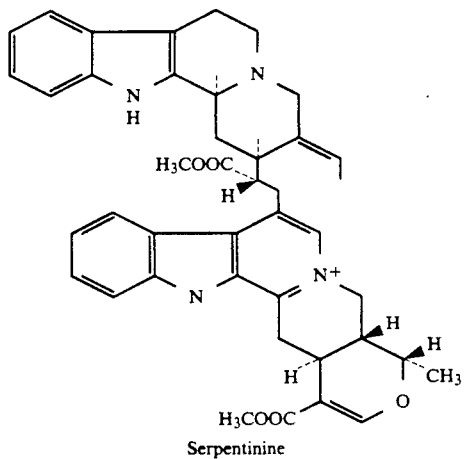
Serpentinine
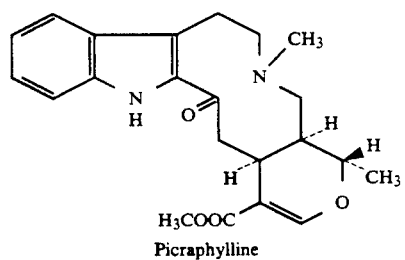
Picraphylline
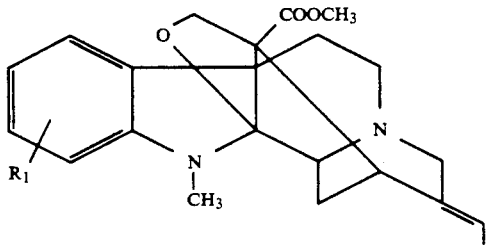
Picraminine, R₁ = alstonine
akuacristine, R₁ = akuammicine
-continued
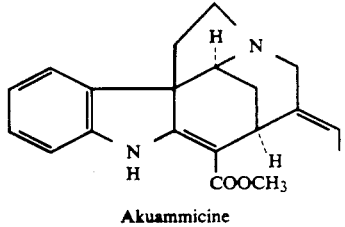
Akuammicine
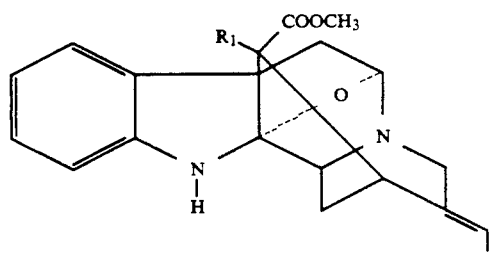
R₁ = H, Picrinine
R₁ = CH₂OCOCH₃, Picraline
R₁ = CHO, Picralinal
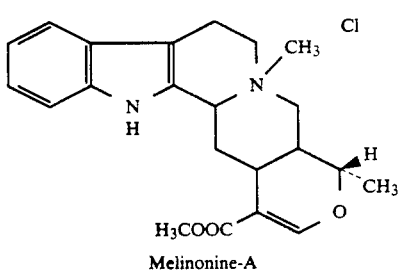
Melinonine-A
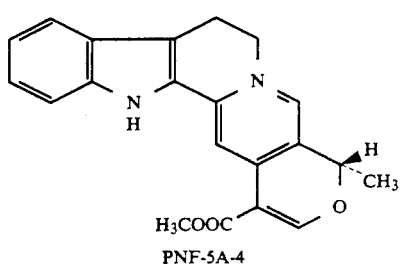
PNF-5A-4
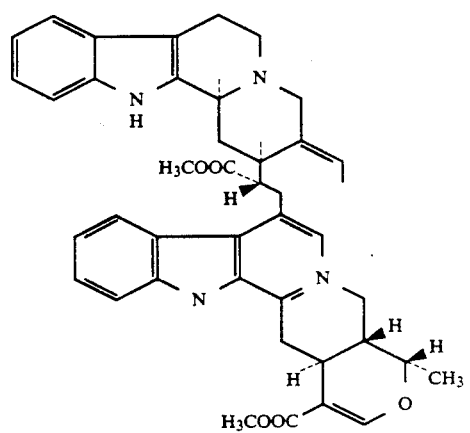
Serpentinine

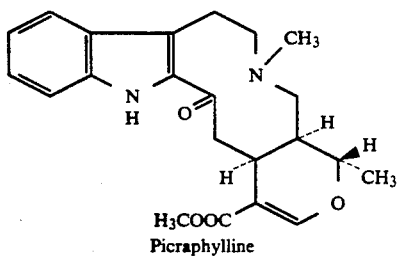
Picraphylline

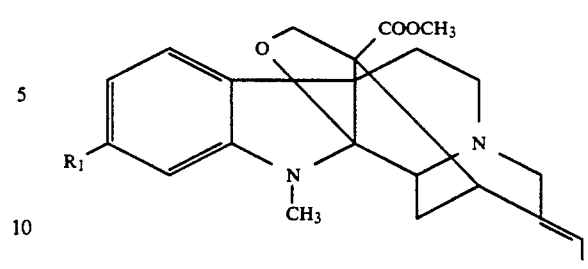

| | IC₅₀ (ug/ml) | |
|---|---|---|
| | W-2 | D-6 |
| R₁ = H, ψ-Akuammigine | 0.10 | 0.83 |
| R₁ = OCH₃, Akuammine | 0.66 | 0.95 |

ANTIMALARIAL IN VITRO BIOASSAY METHOD

The in vitro assays were performed by using a modification of the semi-automated microdilution technique described earlier (Desjardins et al., 1979; Milhous et al., 1985). Two *P. falciparum* malaria parasite clones, designated as Indochina (W-2) and Sierra Leone (D-6), were utilized in susceptibility testing. The W-2 clone is resistant to chloroquine, pyrimethamine, sulfadoxine, and quinine, and the other clone is resistant to mafloquine.

The test extracts were dissolved in DMSO and serially diluted with media. The uptake of tritiated hypoxanthine was used an an index of inhibition of parasite growth.

TABLE 4

IN VITRO ANTIMALARIAL ACTIVITY OF *PICRALIMA NITIDA* EXTRACTS AGAINST W-2 AND D-6 CLONES OF *PLASMODIUM FALCIPARUM*

| | | | IC₅₀, μg/ml | |
|---|---|---|---|---|
| Extract | Plant Part | Solvent | W-2 Clone | D-6 Clone |
| 1 | Seeds | CH₂Cl₂ | 5.15 | 5.03 |
| 2 | Seeds | CH₃OH | 7.35 | 12.99 |
| 3 | Seeds | H₂O | 17.40 | 12.15 |
| 4 | Fruit rind | CH₂Cl₂ | 1.61 | 2.41 |
| 5 | Fruit rind | CH₃OH | 20.79 | 32.16 |
| 6 | Stem bark | CH₂Cl₂ | 6.46 | 14.86 |
| 7 | Seeds | Pet. ether | 22.81 | 25.87 |
| 8 | Seeds | CH₃OH[a] | 0.54 | 0.79 |
| 9 | Stem bark | CH₃OH[a] | 2.00 | 1.23 |
| 10 | Fruit rind | CH₃OH[a] | 2.16 | 1.59 |

[a] Alkaloid fraction

TABLE 5

IN VITRO ANTIMALARIAL ACTIVITY OF *PICRALIMA NITIDA* ALKALOIDS AGAINST W-2 AND D-6 CLONES OF *PLASMODIUM FALCIPARUM*

| | IC₅₀, μg/ml | |
|---|---|---|
| COMPOUND | W-2 Clone | D-6 Clone |
| Alstonine | 0.09 | 0.02 |
| Alstonine (tetrahydro-) | 2.86 | 2.76 |
| Akuammine | 0.66 | 0.95 |
| Ψ-Aukuammigine | 0.10 | 0.83 |
| Picraline | 0.53 | 0.78 |
| Akuammicine | 0.73 | 0.45 |
| Echitamine | 7.25 | 4.68 |
| Yohimbine | 6.16 | 7.51 |
| PNF-S7 | 10.60 | 7.60 |
| Sarpagine | 29.17 | 16.65 |
| Ajmaline | 1.24 | 4.70 |
| NS-6A | 0.003 | 0.002 |
| Chloroquine | 0.04 | 0.006 |
| Artemisinin | 0.002 | 0.004 |
| Quinine | 1.20 | 0.005 |

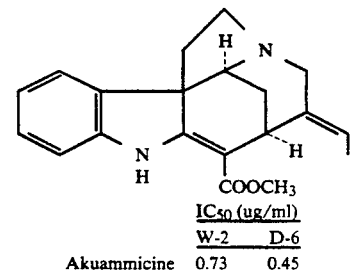

| | IC₅₀ (ug/ml) | |
|---|---|---|
| | W-2 | D-6 |
| Akuammicine | 0.73 | 0.45 |

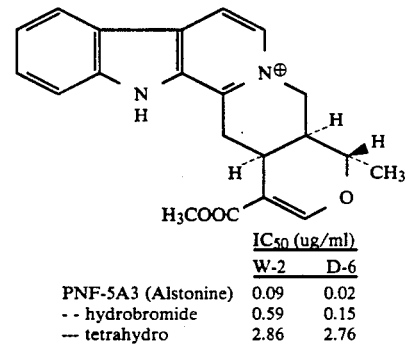

| | IC₅₀ (ug/ml) | |
|---|---|---|
| | W-2 | D-6 |
| PNF-5A3 (Alstonine) | 0.09 | 0.02 |
| - - hydrobromide | 0.59 | 0.15 |
| --- tetrahydro | 2.86 | 2.76 |

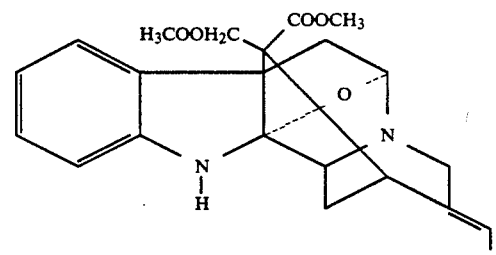

| | IC₅₀ (ug/ml) | |
|---|---|---|
| | W-2 | D-6 |
| Picraline | 0.53 | 0.78 |

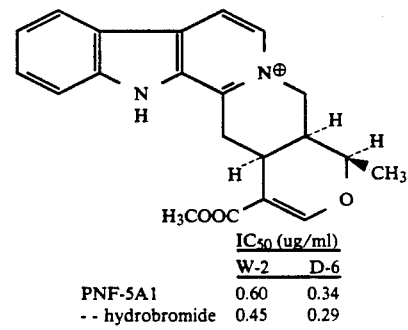

| | IC₅₀ (ug/ml) | |
|---|---|---|
| | W-2 | D-6 |
| PNF-5A1 | 0.60 | 0.34 |
| - - hydrobromide | 0.45 | 0.29 |

-continued

PNF-S7

| | IC$_{50}$ (ug/ml) | |
|---|---|---|
| | W-2 | D-6 |
| PNF-S7 | 10.6 | 7.6 |

Yohimbine

| | IC$_{50}$ (ug/ml) | |
|---|---|---|
| | W-2 | D-6 |
| Yohimbine | 6.16 | 7.51 |

EVALUATION OF PLANT EXTRACTS FOR ANTILEISHMANIAL ACTIVITY USING A MECHANISM BASED RADIORESPIRATORY MICROTECHNIQUE (RAM)

Radiorespirometric microtest based on in vitro inhibition of catabolism of $^{14}CO_2$ of a battery of $^{14}CO_2$ substrates by promastigotes, has been used to examine extracts of 11 plants used in Nigerian traditional medicine for possible antileishmanial activity. Of 13 methanol extracts tested, 5 from *Gongronema latifolia, Dorstenia multiradiata, Picralima nitida, Cola attiensis*, and *Desmodium gangeticum*, were active at concentrations of 50 μg/ml or less against visceral Leishmania isolate.

INTRODUCTION

Infections due to protozoa of the genus Leishmania are a major world-wide health problem, with high endemicity in developing countries. The global prevalence of leishmaniases in man is about 12 million cases, with an estimated incidence of 2-3 million cases per annum. The pathological effects of the disease are complex manifesting in various forms, ranging from self-healing cutaneous lesions; recurrent leishmaniasis recidivans; disfiguring mucocutaneous and diffuse cutaneous diseases; to fatal systemic infection, visceral leishmaniasis or kala azar. In the later form, the reticuloendoethelial system is infected with the resultant toll on the spleen, liver, bone marrow, lymph glands, and, often, some degree of intestinal tract dysfunction. Approximately 350 million people within 80 countries are threatened by the disease worldwide.

Clinical drug intervention is presently limited to the use of pentavelent antimonials (SbV), sodium stilboglu-conate and N-methylglucamine antimonate, and, secondarily, amphotericin or pentamidine. These antileishmanials require parenteral administration with clinical supervision or hospitalization during treatment because of the severity of possible toxic side-effects that include cardiac and/or renal failure. Treatment with the aforementioned agents is not consistently effective particularly for the most virulent leishmanial disease forms.

The World Health Organization has reported large scale resistance of kala azar to SbV, which are the preferred chemotherapy for treatment of most forms of leishmanial disease[36]. In some endemic regions, it has been observed that prolonged medication (22 months or more) with SbV is required to effect a clinical cure[37]. Long term SbV therapy, however, is not usually advocated due to the mentioned cardiac and renal toxicity of SbV. There is, therefore, a need for the development of more effective, less toxic and orally active antileishmanial agents.

[36] Anonymous (1990) Antimonials: large-scale failure in leishmaniasis "alarming". Trop Dis Rsch News (World Health Organization Special Program for Research and Training in Tropical Diseases) 34:1&7.
[37] Bryceson, A. (1987) Therapy in man. Peters, W., Killick-Kendrick, R., eds, *The Leishmaniases in Biology and Medicine*, Vol. 2, New York: Academic Press, pp. 847-907.

Development of a new drug for the treatment of leishmaniasis has been impeded by the lack of a simple, rapid and universally applicable (to the various Leishmania species/strains infecting humans) drug evaluation system[38]. The lack of progress in the development of new antileishmanial agents is evident by the fact that all the clinically useful drugs were developed between 1947 and 1959[39]. Current methods for screening potential antileishmanial agents generally utilize intracellular amastigotes (the mammalian intracellular form) since promastigotes (monoflagellate forms found within the insect vector and culture in vitro) are reported "insensitive" within in vitro assays to SbV compounds used for human leishmaniases[40]. Since there is no system yet available for culturing amastigotes extracellularly except re-isolation from infected tissues and macrophage cultures, their mass culture is rather limited, thereby making them unsuitable for primary screening of potential antileishmanial agents.

[38] Croft, S. L. (1986) In vitro screens in the experimental chotherapy of leishmaniasis and trypanosomiasis. Parasi Today 2:64-69. Neal, R. A. (1987) Experimental chemotherapy. Peters, W., Killick-Kendrick, R., eds, *The Leishmaniases in Biology and Medicine*, Vol. 2, New York: Academic Press, pp. 793-845.
[39] Ibid.
[40] Ibid.

An in vitro radiorespirometric microtest using promastigotes has been developed which relies on drug inhibition of parasite production of $^{14}CO_2O3$ ʌ +3* ʌ U ʌʌ tery of $^{14}C$-substrates by promastigotes to detect drug-mediated parasite damage at low drug concentration within a short time[41]. The test is quantitative, rapid, consistent, and conducted in a serum-free chemically defined medium in which prior adaptation is not necessary to cultivate the so-called "difficult to grow" species. The method has been shown to correlate to patients response to SbV therapy[42].

[41] Jackson, J. E., Tally, J. D., Tang, D. B. (1989) An in vitro micromethod for drug sensitivity testing of Leishmania. Am J Trop Med Hyg 41:318-330. Jackson, J. E., Tally, J. D., Ellis, W. Y., Membrahtu, Y. B., Lawyer, P. G., Were, J. B., Reed, S. G., Panisko, D. M., Limmer, B. L. (1990) Quantitative in vitro drug potency and drug susceptibility evaluation of Leishmania spp. from patients unresponsive to pentavelent antimony therapy. Am J Trop Med Hyg 43:464-480.
[42] Ibid.

Visceral leishmaniasis is endemic to the central Nigerian highlands, and zoonotic cutaneous leishmaniasis, prevalent in the northern half of the country. Because of limited supply, expense and toxicity of commercial antileishmanials, traditional herbal therapy is frequently utilized in many leishmanial endemic regions of Nigeria.

In this study, we have used the radiorespirometric microtest (RAM) to evaluate extracts of 11 plants used in Nigerian folk medicine as antiparasitic remedies for possible antileishmanial activity.

MATERIALS AND METHODS

Plant Materials

Plants were selected from a collection made as part of a Salvage Ethnography Project, Institute of African Studies, University of Nigeria Nsukka. Samples were authenticated by Dr. C. O. Okunji of the Department of Pharmacognosy, University of Nigeria Nsukka and Mr. F. Ozioko of the Department of Botany of the same University. Voucher specimens have been deposited in the Pharmacy Herbarium of the University of Nigeria Nsukka.

Extraction Procedure

Two hundred grams of powdered material from each plant was percolated with 80% methanol and concentrated to a sticky gum under reduced pressure. The extracts from the seed materials were pationed between chloroform and water and the two fractions submitted to bioassay. The list of extracts prepared and the laboratory codes are shown in Table 1.

TABLE 6

| Species | Plant Family | Plant Part | Solvent | Test Code |
|---|---|---|---|---|
| *Afromomum danielli* | Zingiberaceae | Rhizome | MeOH | ADF |
| *Cola attiensis* | Sterculiaceae | Seed | $CH_2Cl_2$ | CT-1 |
|  |  |  | MeOH | CT-2 |
| *Crescentia cujeta* | Bignoniaceae | Fruit | MeOH | CCX |
| *Desmodium gangeticum* | Fabaceae | Leaf | MeOH | SM |
| *Dorstenia multiradiata* | Moraceae | Leaf | MeOH | DL |
| *Dracaena mannii* | Agavaceae | Leaf | MeOH | DM |
| *Garcinia kola* | Guttiferae | Seed | MeOH | GKX |
| *Gongronema latifolia* | Asclepiadaceae | Leaf | MeOH | GG |
| *Picralima nitida* | Apocynaceae | Seed | $CH_2Cl_2$ | HB |
|  |  |  | MeOH | PN |
| *Rothmania withfieldii* | Loganiaceae | Fruit | MeOH | RQ |
| *Schumaniophyton magnificum* | Loganiaceae | Leaf | MeOH | SCM |

Leishmania species/strains

A clinical isolate of visceral *Leishmania (Leishmania) chagasi*, MHOM/BR/84/BA-13, was used for this study. This isolate was selected because sensitivity to SbV was previously determined using RAM. MHOM/BR/84/BA-13 is sensitive to Pentostam (sodium antimony gluconate) at 6 μg/ml Sb (20 μg/ml drug); and to Glucantime (N-methyl-glucamine antimoniate) at 80 μg/ml Sb (286 μg/ml drug)

Cultivation Medium

Promastigotes of *L. chagasi* were grown in a serum-free, defined medium, MM2[43]. The MM2 medium contained 120 μg/ml protein (10 μg/ml human transferrin, 10 μg/ml human insulin, 100 μg/ml defatted bovine albumin), plus 10 μg/ml low density bovine lipoprotein. Previous research demonstrated the need for low protein-serum-free medium because serum protein:drug association reduces in vitro antiparasite activity[44]. Cultures were maintained at 25° C. during growth and incubation with drug.

[43] Op. cit. Jackson et al (1989).
[44] Ibid.

14C-Substrates

The $^{14}C$-labelled substrates and commercial sources are listed in Table 2. For use in radiorespirometry, the $^{14}C$-substrates were diluted to a final concentration of 100,000 disintegrations per minute (dpm)/25 μl using a phosphate buffered balanced salt solution (PBSS: NaCl 6.58 g, KCl 0.4 g, $CaCl_2$ 0.14 g, $KH_2PO_4$ 0.06 g, $MgSO_4$ 0.05 g, sodium phosphate 0.01 M, made up to 1 l with sterile glass-distilled $H_2O$, final pH 7.4). The $^{14}C$-substrates were filter sterilized (0.22 μm Acrodisc filter, Millipore Corporation, Bedford, Mass.) into sterile screwcap vials and stored at 4° C. until use. Subsequent to sterilization, $^{14}C$-substrate vials were opened only within a laminar hood.

Radiorespirometric procedure

Promastigotes were maintained in log phase growth for 3 successive transfers (48–72 hours apart) prior to radiorespirometric testing. Test extracts (or PBSS plus drug solvent [DMSO], for parallel control cultures) was added 24 hours after the third promastigote transfer to fresh growth medium. Incubation in the presence of plant extracts was continued for 96 additional hours while the parasites remained in mid-log phase growth. The rest of the radiorespirometric procedure was conducted as previously described[45].

[45] Ibid.

To each well of a microtiter tray (Biospherics Type T010+C010, Universal Plastics & Engineering Company, Rockville, Md.) were added 25 μl of a single $^{14}C$-substrate (100,000 dpm). The tray was covered with a friction-fit lid to prevent evaporation while the promastigotes were being 3×centrifugally (700×G, 10 min, 4 C) washed free of nutrient medium and drug using PBSS. The final organism pellet was resuspended to a concentration of $1 \times 10^9$ organisms/ml in PBSS. After the addition of 25 μl of organism suspension to each well (total volume per well, 50 μl $^{14}C$-substrate +promastigote suspension), the wells were immediately covered with a filter paper disc (22mm, #410, Schleicher & Schuell, Inc.,Keene, N.H.) which had been premoistened with one drop of saturated $Ba(OH)_2$ solution. The trays were recovered with the lid. If during the 30 minute incubation at 33° C., the Leishmania metabolize the $^{14}C$-substrates to $^{14}CO_2$, the radioactive gas was collected as a $Ba^{14}CO_3$ precipitate on the filter paper discs. After the incubation, the filter discs were removed from the trays, dried using an infrared lamp, and the $^{14}C$ quantity determined using an argon:methane (P10 mixture 9:1 v/v, respectively) gas-flow proportional counter (model 5100, Tennelec, Inc., Oakridge, Tenn.). Data (dmp corrected for background, 1 count per minute; and machine efficiency) were electronically sent to a computer for analysis and graphic presentation.

To obtain a quantitative measure of replicate test variability, tests were initially repeated in duplicate on 4–5 separate days (8–10 tests/drug concentration/organism). The mean dpm/$^{14}C$-substrate had a linear relationship to the magnitude of the standard deviation (SD) in our previous study[46]. It was established from the analysis of previous data on the test system that a linear relationship between dpm and SD, existed. Thereafter testing was only repeated in quadruplicate (duplicate tests on two separate days), for each test extract or control compound.

[46] Ibid.

Drug test procedure

The procedure was conducted as described[47] at the extract concentration of µg/ml. A flow chart and diagram of the test method are shown (FIGS. 1 & 2). Drug sensitivity or resistance to SbV drugs was based on $^{14}C$-substrate(s) (Table 1) for which $^{14}CO_2$ release was decreased for drug-treated parasites compared to parallel tests of phosphate buffered balanced salt solution (PBSS+DMSO)-treated (=drug vehicle) controls.
[47] Ibid.

Each expirement consisted of parallel: (a) duplicate tests of drug-treated parasites; plus (b) duplicate tests of drug vehicle control-treated parasites; plus (c) one "nonbiological" sterility control. The nonbiological control consisted of each \14/C-substrate (one substrate per microtiter tray well), and PBSS (the same PBSS batch used to wash, to suspend the parasites, and to make drug solution). Since there were no parasites in the nonbiological control, any \14/CO/2\ detected was attributed either to biologic (or, less likely, chemical-) contamination of the \14/C-substrates resulting in breakdown of the \14/C-substrates. If radioactivity above background (=10 disintegration per minute, dpm) was detected in the nonbiological control, the suspect solution(s) was replaced and the experiment was repeated.

PLANTS WITH IN VITRO ANTILEISHMANIAL ACTIVITY

| Species | | Plant Part | Test Code |
|---|---|---|---|
| 1. | *Afromomum danielli* | rhizome | ADF |
| 2. | *Cola attiensis* | seed | CT* |
| 3. | *Crescentia cujeta* | fruit | CCX |
| 4. | *Desmodium gangeticum* | leaf | SM* |
| 5. | *Dorstenia multiradiata* | leaf | DL* |
| 6. | *Draceana manii* | leaf | DM |
| 7. | *Garcinia kola* | seed | GKX |
| 8. | *Gongronema latifolia* | leaf | GG* |
| 9. | *Picralima nitida* | fruit | HB* |
| 10. | *Rothmania withfieldii* | fruit | RQ* |
| 11. | *Schumaniophyton magnificum* | leaf | SCM |

TABLE 7

Numeric code abbreviations of $^{14}C$-substrates used for drug tests*

| Numeric Code | 14C-Substrates+ | Commercial Source |
|---|---|---|
| 2 | L-Arginine (guanido-14C) | A++ |
| 3 | L-Aspartic Acid (4-14C) | A |
| 4 | L-Asparagine (U-14C) | A |
| 5 | L-Glutamic Acid (U-14C) | A |
| 6 | L-Glutamine (U-14C) | A |
| 7 | Glycine (U-14C) | A |
| 9 | L-Isoleucine (U-14C) | A |
| 10 | L-Leucine (1-14C) | A |
| 12 | L-Methionine (1-14C) | A |
| 13 | L-Orithine (1-14C) | A |
| 15 | L-Proline (U-14C) | A |
| 17 | Taurine (U-14C) | A |
| 18 | L-Threonine (U-14C) | A |
| 20 | Tyramine (7-14C) | A |
| 24 | L-Fucose (1-14C) | A |
| 25 | D-Galactose (1-14C) | A |
| 28 | D-Mannose (1-14C) | A |
| 42 | Orotic Acid (carboxyl-14C) | N## |
| 44 | Succinic Acid (1,4-14C) | N |
| 46 | Na-n-Butyric Acid (1-14C) | A |
| 49 | D-Glucosamine (1-14C) | A |
| 52 | Na-Glycocholic Acid (1-14C) | A |

TABLE 7-continued

Numeric code abbreviations of $^{14}C$-substrates used for drug tests*

| Numeric Code | 14C-Substrates+ | Commercial Source |
|---|---|---|
| 53 | L-Methionine (methyl-14C) | A |

*All 14C-substrates were selected with specific activities as close to 50 mCi/mM/-carbon atom as obtainable from commercial sources.
+A "U" in the 14C designation indicates a "uniform" 14C-label at each carbon atom in the molecule.
++Amersham, Arlington Heights, IL
New England Nuclear, Boston, MA

RESULTS

At a concentration of 50 µg/ml, 5 of the 11 plant extracts tested inhibited the catabolism of two or more of the substrates to $CO_2$ (Table 3). *Cola attiensis* extract (CT) inhibited parasite catabolism of 5 of the 21 substrates used in the assay, with the strongest activity observed on the disintegration of ornithine, L-proline, L-aspartic acid (FIG. 1). Gongronema (GG) displayed strong inhibition of the catabolism of succinic acid, D-galactose, D-mannose, L-aspartic acid, L-glutamine and D-glucosamine, as well as L-proline, Na-n-butyric acid, and L-gultamic acid (FIG. 2.). For Picralima extract (HB), the strongest activity was observed against butyric acid, with the drug treated parasite cultures showing a suppression of more than 90% when compared with the values observed for the controls. Strong activity was also recorded for succinic acid, glycine and aspartic acid, and inhibition rate of 40% or more was observed with glutamic acid, glutamine, and methionine (FIGS. 3A-3D). No significant inhibition occurred in the catabolism of tyramine, taurine and fucose at the dose of HB tested.

The extract of Dorstenia (DL) strongly inhibited the catabolism of ornithine, butyric acid, and mannose (FIGS. 4A-4C). Moderate inhibition was observed on aspartic acid, glutamic acid, and threonine. The extract, however, caused an enhancement in the catabolism of fucose, succinic acid, and leucine. Desmodium extract (SM) showed strong inhibition of 5 of the 17 substrates used in the study, with the strongest inhibition observed against arginine and L-fucose.

Diseases due to protozoal infections are largely a problem of developing countries. Because of the unavailability of effective and affordable drugs, many of the people in the leishmaniases endemic areas rely on tradidional systems of medicine for treatment. Scientific evaluation of medicinal plants used in the preparation of such traditional remedies are useful in the search for more effective and less toxic therapeutic agents. Plants used for this study were selected from a list of plants used in traditional medicine in Nigeria for the treatment of parasitic infections. Nigeria has an extensive history of successful treatment of native leishmanial and other protozoan diseases using traditional medicines from native plants. Nigerial antiparasitic plant extracts are locally available, inexpensive, administered orally, and have a long precedent of human use because of effectiveness and low adverse reaction.

The results show that the extracts could be explored as sources of leads for new antileishmanial agents. The extracts displayed varied inhibition patterns which suggests different mechanisms in their mode of action.

Two of the extracts, CT and DL appear to be more active against amino acid catabolism, whereas HB, SM and GG showed preferential inhibition against sugars and fatty acids.

One of the plants investigated, *Cola attiensis* is used, among other things, for the treatment of migraine, bronchitis, and catarrh. *Picralima nitida* has been employed in the treatment of malaria, African sleeping sickness, and bacterial infection. *Desmodium gangeticumis* reputed in folk medicine as a very effective antifungal agent, antiviral, anti-inflammatory, and as an oral remedy for various parasitic skin infections. Aqueous decoction of *Dorstenia multiradiata* is used as an antiviral agent as as a local anti-inflammatory Gongronema is valued as a bitter tonic, and the alcoholic infusion is dispensed for bilharzia, viral hepatitis and as a general antimicrobial agent.

Pentavelent antimonials have a serum half-life of 2 hours with the maximum achievable serum level of approximately 20 μg/ml Sb (or approximately 73 μg/ml drug)[48]. It is interesting to note that even as crude mixtures, the 5 active plant extracts (Table 3, FIGS. 1-5) were active at 50 μg/ml and one, DL-55, retained antileishmanial activity to 5 μg/ml. Crude extract antileishmanial activity, at drug concentrations comparable to SbV, seems to indicate high potential fo the active drug principles as a new antileishmanials.

[48] Chulay, J. D., Fleckenstein, L., Smith, D. H. (1988) Pharmacokinetics of antimony during treatment of visceral leishmaniasis with sodium stibogluconate or meglumine antimoniate. Trans Roy Soc Trop Med Hyg 82:69–72.

The plants are presently being analyzed for their chemical constituents. Literature, however, revealed that the plants vary in their constituents. *P. nitida* contains indole alkaloids as the major components[49], D. gangeticum yields β-carbolines and phenylethylamines[50]. There is no available report on any previous chemical analysis of *Cola attiensis, Gonoronema latifolia*, or *Dorstenia multiradiata*.

[49] Saxton, J. E. (1973) Alkaloids of Picralima and Alstonia species. In: R. H. F. Manske (Ed.) The Alkaloids - Chemistry and Physiology, Academic Press, New York. p. 157–179.
[50] Oliver-Bever, B. (1986) Medicinal Plants in tropical West Africa, Cambridge University Press, London, p. 102.

NOVEL ANTILEISHMANIAL INDOLE ALKALOIDS FROM FRUITS OF PICRALIMA NITIDA

Methanol and aqueous extracts of the West African tree *Picralima nitida* showed significant inhibition of leishmania promastigotes. Using a radiorespirometric microtest based on in vitro inhibition of catabolism of \14/CO/2 \ of a battery of \14/C-substrates by promastigotes, the extracts were found active at concentrations of 50 μg/ml or less against visceral *Leishmania chagasi* and cutaneous *L. mexicana*. The extracts significantly inhibited (10%–90%) the catabolism of certain sugars, amino acids, or fatty acid precursors by promastigotes. The indole alkaloids akuammine, pseudoakuammigine, picraline, alstonine and akuammicine were isolated from the active fraction. The greatest inhibition was observed with alstonine. The compound a dose related activity with the highest growth inhibition observed at 50 μg/ml. At 20 μg/ml the compound showed a growth of 69.3% after 96 hours.

*Leishmania (Leishmania) chagasi*, MHOM/BR/84/BA-13, MM2 medium, 96 hrs HB-1 Plant Extract (20 μg/ml), Orig. File: 910625HB, 10-9 pros/ml, DMSO final concentration 0.58%

| $^{14}$C-SUB-STRATES | CONTROL MEAN n = 8 | CONTROL SDEV | TEST MEAN n = 3 | TEST SDEV |
|---|---|---|---|---|
| L-Aspartic Acid (4-$^{14}$C) | 9,322 | 2,318 | 18,972 | 3,593 |
| L-Glutamine (U-$^{14}$C) | 1,519 | 260 | 2,771 | 834 |
| L-Glycine (U-$^{14}$C) | 209 | 98 | 163 | 130 |
| L-Ornithine (1-$^{14}$C) | 698 | 162 | 1,084 | 53 |
| Succinic Acid (1,4-$^{14}$C) | 330 | 67 | 216 | 58 |
| Na-n-Butyric Acid (a-$^{14}$C) | 1,172 | 225 | 406 | 35 |

NOTE:
Growth inhibition over 96 hours was 69.3%: Control cells were $3.12 \times 10^7$ pros/ml ($624 \times 50,000$), whereas HB-1-treated were $0.96 \times 10^7$ pros/ml ($192 \times 50,000$, 30.7% Control). Pentavelent antimonials do not produce visible growth inhibition at 20 μg/ml Sb (73 μg/ml drug)!

*Leishmania (Leishmania) chagasi*, MHOM/BR/84/BA-13, MM2 medium, 96 hrs HB-1 Plant Extract (10 μg/ml), Orig. File: 910619HB, 10-9 pros/ml, DMSO final concentration 0.58%

| $^{14}$C-SUB-STRATES | CONTROL MEAN n = 4 | CONTROL SDEV | TEST MEAN n = 4 | TEST SDEV |
|---|---|---|---|---|
| L-Aspartic Acid (4-$^{14}$C) | 24,695 | 7,078 | 24,884 | 3,703 |
| L-Glutamine (U-$^{14}$C) | 6,316 | 718 | 8,069 | 405 |
| L-Glycine (U-$^{14}$C) | 587 | 47 | 536 | 61 |
| L-Ornithine (1-$^{14}$C) | 3,206 | 433 | 5,129 | 543 |
| Succinic Acid (1,4-$^{14}$C) | 313 | 32 | 344 | 87 |
| Na-n-Butyric Acid (a-$^{14}$C) | 3,599 | 149 | 5,080 | 272 |

*Leishmania (Leishmania) chagasi*, MHOM/BR/84/BA-13, MM2 medium, 96 hrs HB-1 Plant Extract (10 μg/ml), Orig. File: 910628HB, 10-9 pros/ml, DMSO final concentration 0.58%

| $^{14}$C-SUB-STRATES | CONTROL MEAN n = 8 | CONTROL SDEV | TEST MEAN n = 8 | TEST SDEV |
|---|---|---|---|---|
| L-Aspartic Acid (4-$^{14}$C) | 11,544 | 3,274 | 12,851 | 1,092 |
| L-Glutamine (U-$^{14}$C) | 2,524 | 533 | 5,084 | 956 |
| L-Glycine (U-$^{14}$C) | 177 | 21 | 226 | 24 |
| L-Ornithine (1-$^{14}$C) | 1,282 | 281 | 3,194 | 400 |
| Succinic Acid (1,4-$^{14}$C) | 280 | 51 | 640 | 105 |
| Na-n-Butyric Acid (a-$^{14}$C) | 2,021 | 571 | 3,296 | 1,256 |

| | CONTROL | | TEST | |
|---|---|---|---|---|
| $^{14}$C-SUB-STRATES | MEAN n = 8 | CONTROL SDEV | MEAN n = 3 | TEST SDEV |
| L-Aspartic Acid (4-$^{14}$C) | 32,733 | 3,503 | 31,073 | 1,693 |
| L-Glutamine (U-$^{14}$C) | 12,389 | 1,932 | 12,453 | 1,210 |
| L-Glycine (U-$^{14}$C) | 681 | 157 | 478 | 49 |
| L-Ornithine (1-$^{14}$C) | 10,399 | 3,090 | 10,560 | 706 |
| Succinic Acid (1,4-$^{14}$C) | 2,550 | 344 | 1,377 | 367 |
| Na-n-Butyric Acid (a-$^{14}$C) | 5,739 | 755 | 6,331 | 398 |

Leishmania (Leishmania) chagasi, MHOM/BR/84/BA-13, MM2 medium, 96 hrs HB-1 Plant Extract (1 μg/ml), Orig. File: 910618HB, 10-9 pros/ml, DMSO final concentration 0.58%

NEW LEADS TO THE TREATMENT OF TRYPANOSOMIASIS BASED ON ISOLATES FROM PLANTS USED IN TRADITIONAL MEDICINE

Available chemotherapeutiv agents for the treatment of trypanosomiases are generally unstaisfactory, as most of the drugs are very toxic and cases of druc resistance are becoming widespread. We have examined extracts of twleve plants used in traditional medicine in South-Eastern Nigeria antiparasitic agents for possible antitrypanosomial activity.

From the in vivo inhibition of the development of Trypanosoma brucei brucei in mice and rats, extracts of two of the species, Picralima nitada, and Dorstenia multiradiata were found active at very low doses.

An intraperitoneal dose of 50 mg/kg and 5 mg/kg of the methanol and aqueous extracts respectively of Picralima seeds completely cleared animals of the parasites at post-treatment day 12 in rats and day 10 in the mouse model. Methanol extract of Dorstenia gave similar results at treatment day 10 and 8 for the rat and mouse models respectively.

The indole alkaloids akuammine, pseudo-akuammigine, picraline, alstonine and akuammicine were isolated from the active fraction of P. nitida, whereas anthocyanidins were the active components of the extract from D. multiradiata.

IN VIVO ANTITRYPANOSOMAL ACTIVITY OF *PICRALIMA NITIDA* EXTRACTS

| Test Substance | Dose | Animal Model | Day of 0% Parasite Count |
|---|---|---|---|
| MeOH Extract | 50 mg | rat | 12 |
| MeOH Extract | 50 mg | mouse | 10 |
| H$_2$O Extract | 5 mg | rat | 12 |
| H$_2$O Extract | 5 mg | mouse | 10 |
| Berenil | 7 mg | rat | 8 |
| Berenil | 7 mg | mouse | 6 |

*Dosing by i.p. route
*Paarasitemia was detected on day 21 after treatment

What is claimed is:

1. Water, methanol and dichloromethane alkaloid extracts from seeds, fruit-rind and stem-bark of plants selected from the group consisting of Picralima nitida, Gongronema latifolia, Rothmania withfieldii and Desmodium gangeticum.

2. An isolated alkaloid from *Picralima nitida* of claim 1, having the formula:

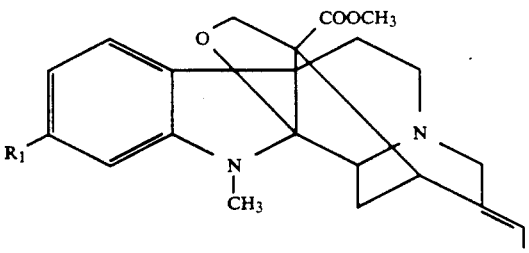

wherein R$_1$ is H.

3. An isolated alkaloid from *Picralima nitida* of claim 1, having the formula:

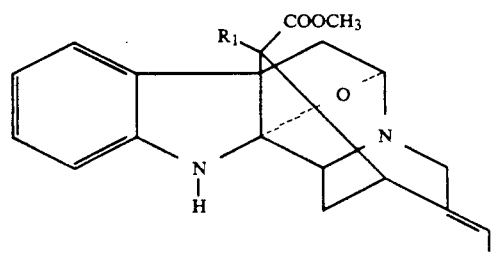

wherein R$_1$ is selected from H and CHO.

4. An isolated alkaloid from *Picralima nitida* of claim 1, having the formula:

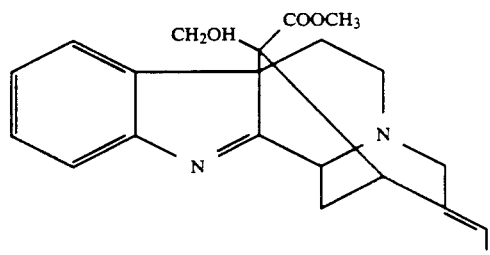

5. An isolated alkaloid from *Picralima nitida* of claim 1, having the formula:

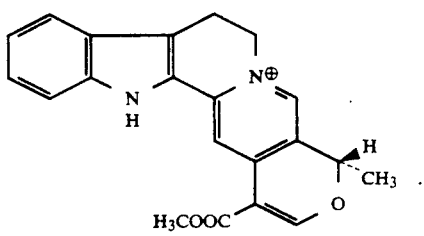

6. An isolated dimer from *Picralima nitida* of claim 1, having the formula:

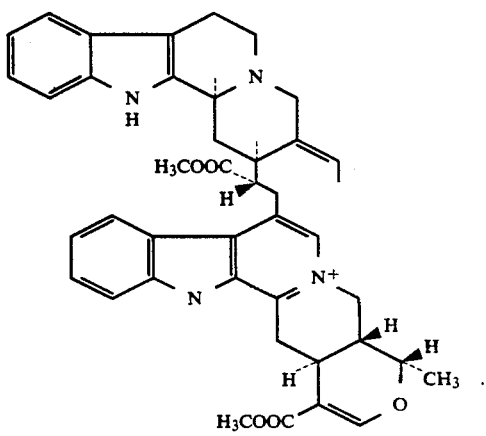

7. An isolated dimer from *Picralima nitida* of claim 1, having the formula:

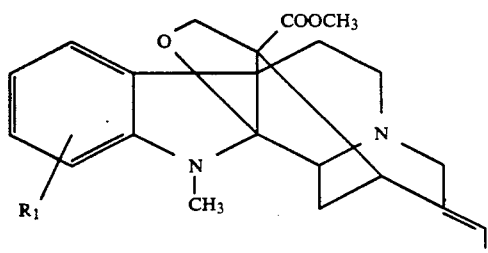

wherein $R_1$ is alstonine.

8. An isolated dimer from *Picralima nitida* of claim 1, having the formula:

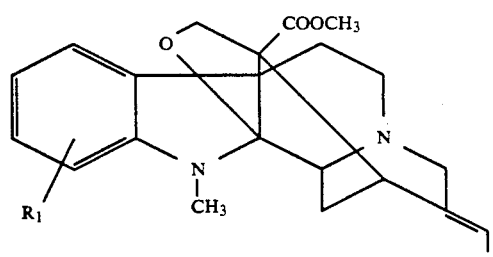

wherein $R_1$ is akuammicine.

9. An isolated alkaloid from *Picralima nitida* of claim 1, having the formula:

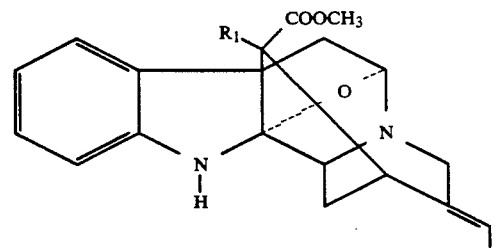

wherein $R_1$ is CHO.

10. A method of preparing substantially purified alkaloids from seeds, fruit-rind and stem-bark of a plant selected from the group consisting of *Picralima nitida, Gongronema latifolia, Dorstenia multiradiata, Cola attiensis, Rothmania withfieldii* and *Desmodium gangeticum*, for use in the treatment of drug resistant strains of protozoal diseases, comprising:

pulverizing said seeds, fruit-rind and stem-bark;

extracting said pulverized seeds, fruit-rind and stem-bark with a first solvent selected from the group consisting of dichloromethane, methanol, petroleum ether and water, drying the extracted material and re-extracting the dried material with a different solvent than said first solvent, wherein said different solvent than said first solvent is selected from a member of the group consisting of said first solvent;

extracting a fresh sample of said seeds, fruit-rind and stem-bark with boiling water;

filtering and concentrating the boiled water solvent extracts under reduced pressure to dryness;

concentrating the dried extract to a gum and re-extracting said gum with an aqueous acidic HCl solution;

filtering the acidic extract and making it alkaline to a pH of about 9 with a concentrated NaOH solution;

extracting the alkaline solution with dichloromethane;

concentrating organic layers of the extracts of alkaline solution to dryness under reduced pressure to obtain an alkaloid fraction; and separating the alkaloid fraction by liquid chromotography-mass spectrometry to obtain substantially purified alkaloids for use in treatment of protozoal diseases.

11. The method of claim 10, wherein said first solvent is selected from the group consisting of water, methanol and dichloromethane, and the protozoal diseases are malaria, leishmaniases and tryponosomiasis.

12. The method of claim 11, wherein said fruit-rind and stem is from *Pricralima nitida*, the substantially purified alkaloids are selected from the group consisting of akuammine, akuammicine, melinonine, picraphylline, picraline, pseudoakuamigine and mixtures thereof, except that said seeds are not used.

13. The process of claim 12, wherein picramimine and akuacristine dimers of said alkaloids are formed.

14. A method of providing inhibitory activity against malarial protozoa in mammals, comprising:

administering an antimalarial amount of an extract of *Picralima nitida* obtained by the process of claim 12.

15. The method of claim 14, wherein said malarial protozoa is a drug resistant clone of *Plasmodium falciparum*.

16. The method of claim 15, wherein doses of said antimalarial alkaloid extract administered is from about 1.23 to about 32 mg/ml.

17. The method of claim 12, wherein the leishmaniases protozoal is visceral *Leishmania chagasi* and *L. mexicana*.

18. The method of claim 12, wherein the alkaloid is alstonine.

19. The method of claim 11, wherein said fruit rind, stem and seed are from *Cola attiensis* and the substantially purified alkaloids exhibit antileishmanial activity in mammals.

20. The method of claim 11, wherein said fruit rind, stem and seed are from *Desmodium gangeticum* and the substantially purified alkaloids exhibit antileishmanial activity in mammals.

21. The method of claim 11, wherein said fruit rind, stem and seed are from *Dorstenia multiradiata* and the substantially purified alkaloids exhibit antileishmanial activity in mammals.

22. The method of claim 11, wherein said fruit rind, stem and seed are from *Gongronema latifolia* and the substantially purified alkaloids exhibit antileishmanial activity in mammals.

23. The method of claim 11, wherein said fruit rind, stem and seed are from *Rothmania withfieldii* and the substantially purified alkaloids exhibit antileishmanial activity in mammals.

24. The method of claim 11, wherein said plant is the fruit rind, stem and seed selected from *Picralima nitida* and *Dorstenia multiradiata* and the substantially purified alkaloids exhibit antitrypanosomial activity in mammals.

25. The method of claim 24, wherein said plant is *Dorstenia multiradiata*, the substantially purified extract is anthocyanidins, and said anthocyanidins exhibit antitrypanosomial activity in mammals.

* * * * *